United States Patent
Okada et al.

(10) Patent No.: US 9,436,105 B2
(45) Date of Patent: Sep. 6, 2016

(54) TRIARYLAMINE DERIVATIVE AND ELECTROPHOTOGRAPHIC PHOTOSENSITIVE MEMBER

(71) Applicant: KYOCERA Document Solutions Inc., Osaka-shi (JP)

(72) Inventors: Hideki Okada, Osaka (JP); Kensuke Kojima, Osaka (JP); Fumio Sugai, Osaka (JP)

(73) Assignee: KYOCERA Document Solutions Inc., Osaka (JP)

( * ) Notice: Subject to any disclaimer, the term of this patent is extended or adjusted under 35 U.S.C. 154(b) by 0 days.

(21) Appl. No.: 14/754,572

(22) Filed: Jun. 29, 2015

(65) Prior Publication Data

US 2015/0378268 A1 Dec. 31, 2015

(30) Foreign Application Priority Data

Jun. 30, 2014 (JP) .................................. 2014-135133

(51) Int. Cl.
  *G03G 5/047* (2006.01)
  *G03G 5/06* (2006.01)
  *C07C 211/54* (2006.01)
  *C07C 217/80* (2006.01)

(52) U.S. Cl.
  CPC ........... *G03G 5/0614* (2013.01); *C07C 211/54* (2013.01); *C07C 217/80* (2013.01); *G03G 5/047* (2013.01); *G03G 5/0618* (2013.01)

(58) Field of Classification Search
  CPC .. G03G 5/0614; G03G 5/047; G03G 5/0618; C07C 211/54; C07C 217/80
  USPC ...................................................... 430/58.85
  See application file for complete search history.

(56) References Cited

U.S. PATENT DOCUMENTS 8,859,818 B2  10/2014  Nakamura et al.
2009/0325096 A1*  12/2009  Wu ..................... G03G 5/0535
                                    430/58.85
2010/0150608 A1*  6/2010  Mitsumori .......... G03G 5/0564
                                    399/159
2012/0022293 A1  1/2012  Nakamura et al.

FOREIGN PATENT DOCUMENTS

JP  2012-027139 A  2/2012

* cited by examiner

Primary Examiner — Peter Vajda
(74) Attorney, Agent, or Firm — Studebaker & Brackett PC

(57) ABSTRACT

A triarylamine derivative is represented by general formula (I). In general formula (I), $R_1$ and $R_2$ each represent, independently of one another, a chemical group selected from the group consisting of a halogen atom, an optionally substituted alkyl group having a carbon number of at least 1 and no greater than 6, an optionally substituted alkoxy group having a carbon number of at least 1 and no greater than 6, and an optionally substituted aryl group having a carbon number of at least 6 and no greater than 12. In general formula (I), m and n each represent an integer of at least 0 and no greater than 4. When m and n represent integers greater than 1, chemical groups $R_1$ bonded to the same aromatic ring and chemical groups $R_2$ bonded to the same aromatic ring may be the same or different to one another.

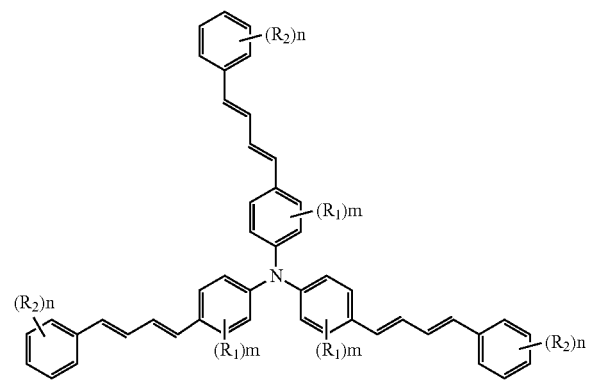

(I)

5 Claims, 7 Drawing Sheets

TRIARYLAMINE DERIVATIVE AND ELECTROPHOTOGRAPHIC PHOTOSENSITIVE MEMBER

INCORPORATION BY REFERENCE

The present application claims priority under 35 U.S.C. §119 to Japanese Patent Application No. 2014-135133, filed Jun. 30, 2014. The contents of this application are incorporated herein by reference in their entirety.

BACKGROUND

The present disclosure relates to triarylamine derivatives and electrophotographic photosensitive members.

Electrophotographic photosensitive members are used as image bearing members in electrophotographic printers and multifunction peripherals. A typical electrophotographic photosensitive member includes a conductive substrate and a photosensitive layer located either directly or indirectly on the conductive substrate. An electrophotographic photosensitive member including a photosensitive layer that contains a charge generating material, a charge transport material, and a resin (organic material) for binding the aforementioned materials is referred to as an organic electrophotographic photosensitive member. An organic electrophotographic photosensitive member in which one layer implements a charge transport function by mainly containing a charge transport material and another layer implements a charge generation function by mainly containing a charge generating material is referred to as a multi-layer electrophotographic photosensitive member. An organic electrophotographic photosensitive member in which one layer includes both a charge transport material and a charge generating material, and thus in which the one layer implements both a charge transport function and a charge generation function, is referred to as a single-layer electrophotographic photosensitive member.

On the other hand, another example of an electrophotographic photosensitive member is an inorganic electrophotographic photosensitive member in which an inorganic material is used (for example, a selenium or amorphous silicon photosensitive member). Advantages of organic electrophotographic photosensitive members as compared to inorganic electrophotographic photosensitive members are relatively small environmental effects and ease of photosensitive layer formation. As a consequence, organic electrophotographic photosensitive members are currently widely used in image forming apparatuses.

Known examples of effective charge transport materials for organic electrophotographic photosensitive members include tris(4-styrylphenyl)amine derivatives.

SUMMARY

A triarylamine derivative according to the present disclosure is represented by general formula (I).

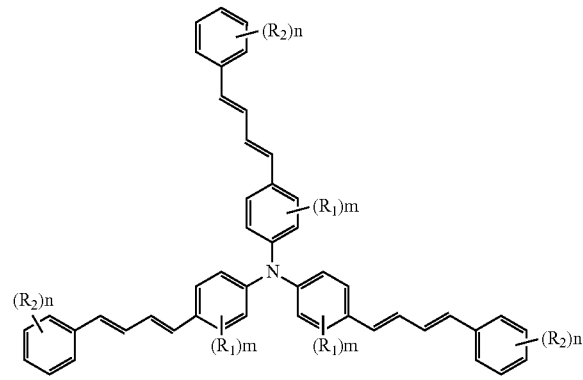

(I)

In general formula (I), $R_1$ and $R_2$ each represent, independently of one another, a chemical group selected from the group consisting of a halogen atom, an optionally substituted alkyl group having a carbon number of at least 1 and no greater than 6, an optionally substituted alkoxy group having a carbon number of at least 1 and no greater than 6, and an optionally substituted aryl group having a carbon number of at least 6 and no greater than 12. In general formula (I), m and n each represent an integer of at least 0 and no greater than 4. When m represents an integer greater than 1, chemical groups $R_1$ bonded to the same aromatic ring may be the same or different to one another. When n represents an integer greater than 1, chemical groups $R_2$ bonded to the same aromatic ring may be the same or different to one another.

An electrophotographic photosensitive member according to the present disclosure includes a photosensitive layer containing a charge generating material and a hole transport material. The photosensitive layer is either one of a multi-layer photosensitive layer and a single-layer photosensitive layer. The multi-layer photosensitive layer includes a charge generating layer that contains the charge generating material and a charge transport layer that contains the hole transport material. In the multi-layer photosensitive layer, the charge transport layer is located on the charge generating layer. The single-layer photosensitive layer contains the charge generating material and the hole transport material. The hole transport material is the triarylamine derivative described above.

DETAILED DESCRIPTION

Figure 1:
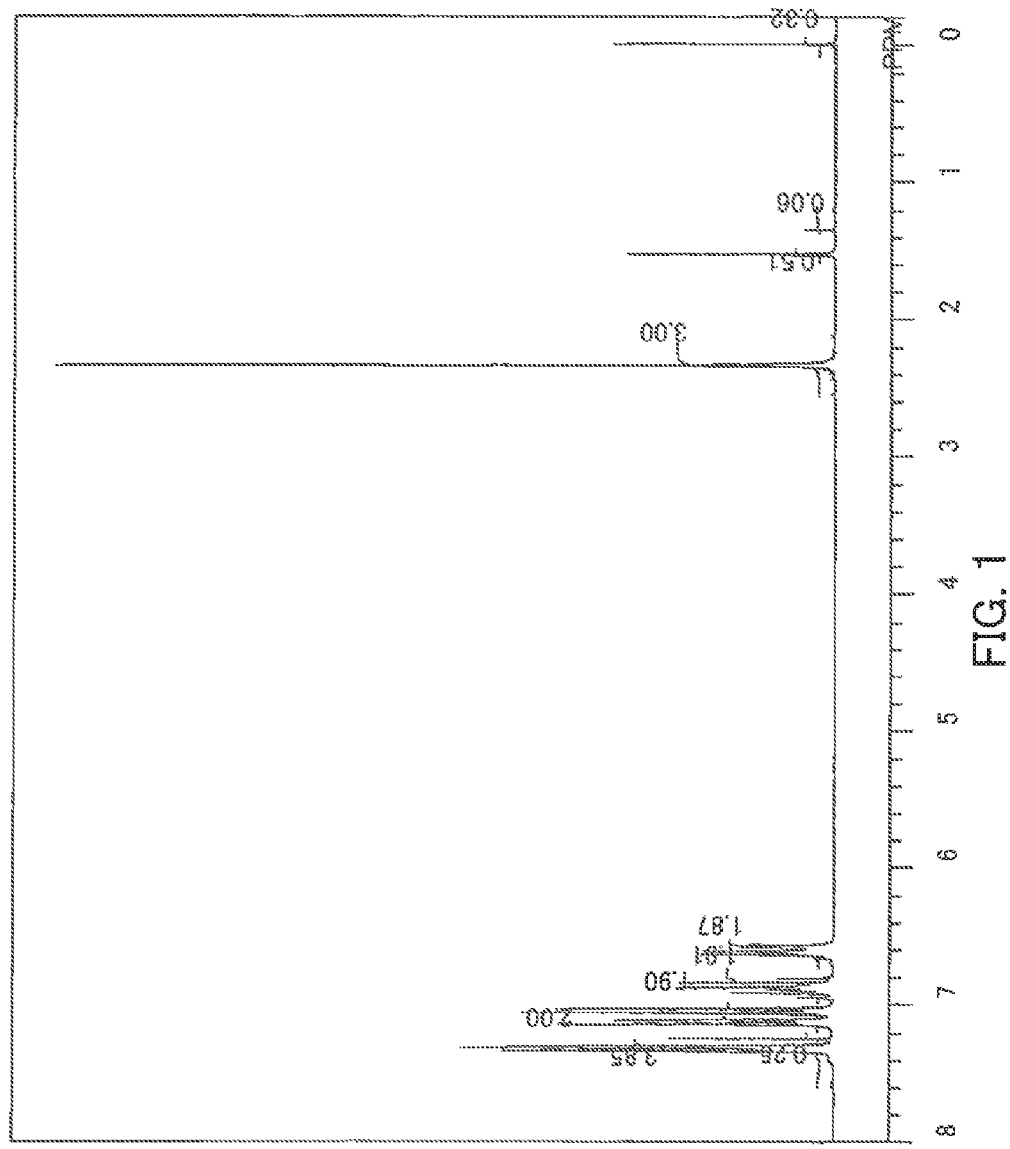
FIG. 1 is a $^1$H-NMR spectrum of a triarylamine derivative represented by formula (HT-1).

The following explains embodiments of the present disclosure in detail, but the present disclosure is not in any way limited by the embodiments described below and appropriate variations may be made in practice within the intended scope of the present disclosure. Note that although explanation is omitted in some places in order to avoid repetition, such omission does not limit the essence of the present disclosure.

In the present description the term "-based" may be appended to the name of a chemical compound in order to form a generic name encompassing both the chemical compound itself and derivatives thereof. Also, when the term "-based" is appended to the name of a chemical compound used in the name of a polymer, the term indicates that a repeating unit of the polymer originates from the chemical compound or a derivative thereof.

First Embodiment

Triarylamine Derivative

A first embodiment of the present disclosure is a triarylamine derivative. The triarylamine derivative according to the present embodiment is represented by general formula (I) shown below.

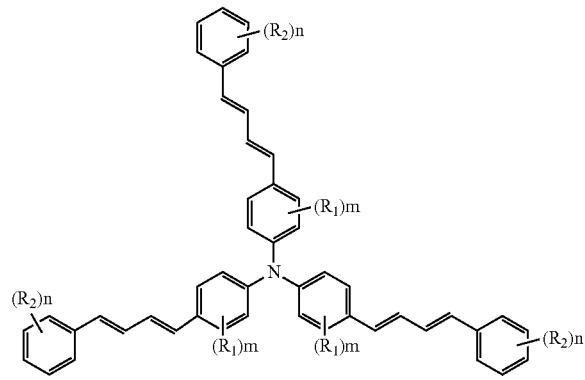

(I)

In general formula (I), $R_1$ and $R_2$ each represent, independently of one another, a chemical group selected from the group consisting of a halogen atom, an optionally substituted alkyl group having a carbon number of at least 1 and no greater than 6, an optionally substituted alkoxy group having a carbon number of at least 1 and no greater than 6, and an optionally substituted aryl group having a carbon number of at least 6 and no greater than 12. Also, in general formula (I), m and n each represent an integer of at least 0 and no greater than 4. When m represents an integer greater than 1, chemical groups $R_1$ bonded to the same aromatic ring may be the same or different to one another. When n represents an integer greater than 1, chemical groups $R_2$ bonded to the same aromatic ring may be the same or different to one another.

The triarylamine derivative represented by general formula (I) shown above (also referred to below as triarylamine derivative (I)) has three phenyl butadienyl groups. A triarylamine derivative having a structure such as described above is thought to have excellent solubility in solvents and compatibility with binder resins. As a result, it is thought that during formation of a photosensitive layer, crystallization of the triarylamine derivative in the photosensitive layer is inhibited. Therefore, it is possible to effectively produce an electrophotographic photosensitive member in which no crystallized portion is readily visible and that has excellent external appearance in terms of a surface thereof.

The triarylamine derivative (I) is thought to have excellent solubility in solvents and compatibility with binder resins in the same way as described above. Therefore, the triarylamine derivative tends to be easily dispersed in a photosensitive layer in a uniform manner. A photosensitive layer having the triarylamine derivative dispersed uniformly therein tends to have excellent electrical properties (in particular, sensitivity properties such as restriction of residual potential). Therefore, it is possible to effectively produce an electrophotographic photosensitive member having excellent electrical properties (in particular, sensitivity properties).

Examples of halogen atoms that may be represented by $R_1$ and $R_2$ in general formula (I) include fluorine (fluoro group), chlorine (chloro group), and bromine (bromo group).

Examples of alkyl groups having a carbon number of at least 1 and no greater than 6 that may be represented by $R_1$ and $R_2$ in general formula (I) include a methyl group, an ethyl group, a propyl group, an isopropyl group, an n-butyl group, a t-butyl group, a pentyl group, an isopentyl group, a neopentyl group, and a hexyl group. Among alkyl groups having a carbon number of at least 1 and no greater than 6, alkyl groups having a carbon number of least 1 and no greater than 3 are preferable, with a methyl group or an isopropyl group being particularly preferable.

Examples of alkoxy groups having a carbon number of at least 1 and no greater than 6 that may be represented by $R_1$ and $R_2$ in general formula (I) include a methoxy group, an ethoxy group, an n-propoxy group, an isopropoxy group, an n-butoxy group, an s-butoxy group, a t-butoxy group, a pentyloxy group, an isopentyloxy group, a neopentyloxy group, and a hexyloxy group. Among alkoxy groups having a carbon number of at least 1 and no greater than 6, alkoxy groups having a carbon number of at least 1 and no greater than 3 are preferable, with a methoxy group being particularly preferable.

Examples of aryl groups having a carbon number of at least 6 and no greater than 12 that may be represented by $R_1$ and $R_2$ in general formula (I) include a phenyl group and a naphthyl group. Aryl groups having a carbon number of at least 6 and no greater than 12 that may be represented by $R_1$ and $R_2$ in general formula (I) may optionally have substituents such as described further below. Examples of substituted aryl groups having a carbon number of at least 6 and no greater than 12 include aryl groups having a carbon number of at least 6 and no greater than 12 and having at least one and no greater than three alkyl groups that each has a carbon number of at least 1 and no greater than 6. Specific examples include a tolyl group, a xylyl group, and a mesityl group.

The alkyl groups having a carbon number of at least 1 and no greater than 6, the alkoxy groups having a carbon number of at least 1 and no greater than 6, and the aryl groups having a carbon number of least 6 and no greater than 12 may be substituted. No particular limitations are placed on possible substituents, but examples thereof include alkyl groups having a carbon number of at least 1 and no greater than 6, alkoxy groups having a carbon number of at least 1 and no greater than 6, and aryl groups having a carbon number of at least 6 and no greater than 12. Examples of alkyl groups having a carbon number of at least 1 and no greater than 6 that may be substituents are the same as the examples given of alkyl groups having a carbon number of at least 1 and no greater than 6 that may be represented by $R_1$ and $R_2$ in general formula (I). Examples of alkoxy groups having a carbon number of at least 1 and no greater than 6 that may be substituents are the same as the examples given of alkoxy groups having a carbon number of at least 1 and no greater than 6 that may be represented by $R_1$ and $R_2$ in general formula (I). Examples of aryl groups having a carbon number of at least 6 and no greater than 12 that may be substituents are the same as the examples given of aryl groups having a carbon number of at least 6 and no greater than 12 that may be represented by $R_1$ and $R_2$ in general formula (I).

When m represents an integer greater than 1, chemical groups $R_1$ bonded to the same aromatic ring may be the same or different to one another. In order to facilitate understanding, an example is explained in which m represents 2 and in which two chemical groups $R_1$ bonded to the same aromatic ring are at an ortho position and a meta position relative to the nitrogen atom bonded to the same aromatic ring. In such a situation, the ortho position $R_1$ and the meta position $R_1$ bonded to the same aromatic ring may be the same or different to one another. However, in the above situation, the ortho position $R_1$ is the same for each of the three aromatic rings bonded to the nitrogen atom. Also, in the above situation, the meta position $R_1$ is the same for each of the three aromatic rings bonded to the nitrogen atom.

When n represents an integer greater than 1, chemical groups $R_2$ bonded to the same aromatic ring may be the same or different to one another. In order to facilitate understanding, an example is explained in which n represents 2 and in which two chemical groups $R_2$ bonded to the same aromatic ring are at an ortho position and a meta position relative to the butadienyl group bonded to the same aromatic ring. In such a situation, the ortho position $R_2$ and the meta position $R_2$ bonded to the same aromatic ring may be the same or different to one another. However, in the above situation, the ortho position $R_2$ is the same for each of the three aromatic rings bonded to the respective butadienyl groups. Also, in the above situation, the meta position $R_2$ is the same for each of the three aromatic rings bonded to the respective butadienyl groups.

Due to the resonance effect of benzene ring electrons, in general formula (I) $R_1$ and $R_2$ preferably each represent, independently of one another, a chemical group selected from the group consisting of an alkyl group having a carbon number of at least 1 and no greater than 6 and an alkoxy group having a carbon number of at least 1 and no greater than 6.

In order to maintain a stable molecular structure, m and n preferably each represent 0 or 1 in general formula (I).

In general formula (I), n preferably represents 1 and the chemical group $R_2$ is preferably located at an ortho or para position relative to the butadienyl group. The above is due to the electron resonance effect of the benzene ring to which $R_2$ is bonded being thought to increase π electron conjugation of the overall molecule.

Specific examples of the triarylamine derivative (I) are shown below by formulae (HT-1) to (HT-7). Compounds represented by formulae (HT-1) to (HT-7) shown below may be referred to below as triarylamine derivatives (HT-1) to (HT-7).

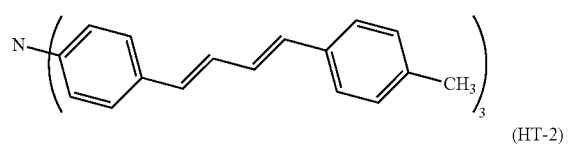

(HT-1)

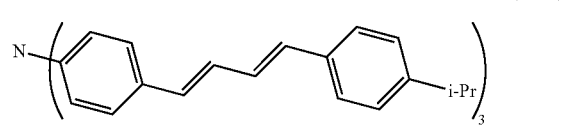

(HT-2)

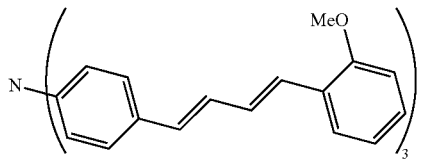

(HT-3)

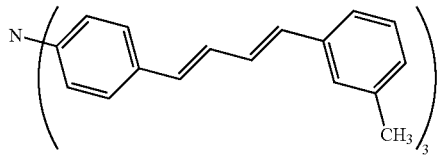

(HT-4)

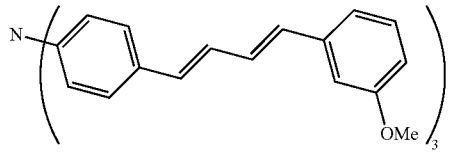

(HT-5)

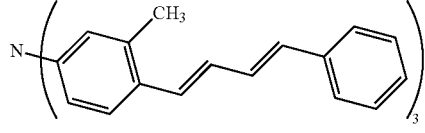

(HT-6)

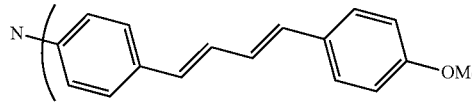

(HT-7)

Among the specific examples shown above for the triarylamine derivative (I), $^1$H-NMR spectra of the triarylamine derivatives (HT-1) to (HT-5) are illustrated by FIGS. 1-5, respectively.

The triarylamine derivative (I) can be produced according to reaction formulae (R-1) to (R-3) shown below, or through a method conforming therewith. In addition to reactions represented by reaction formulae (R-1) to (R-3), other processes may be carried out as appropriate depending on necessity thereof.

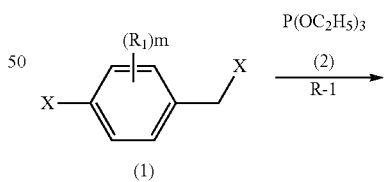

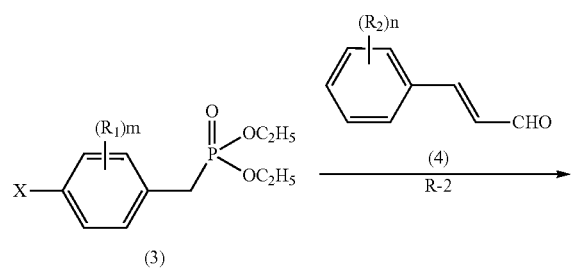

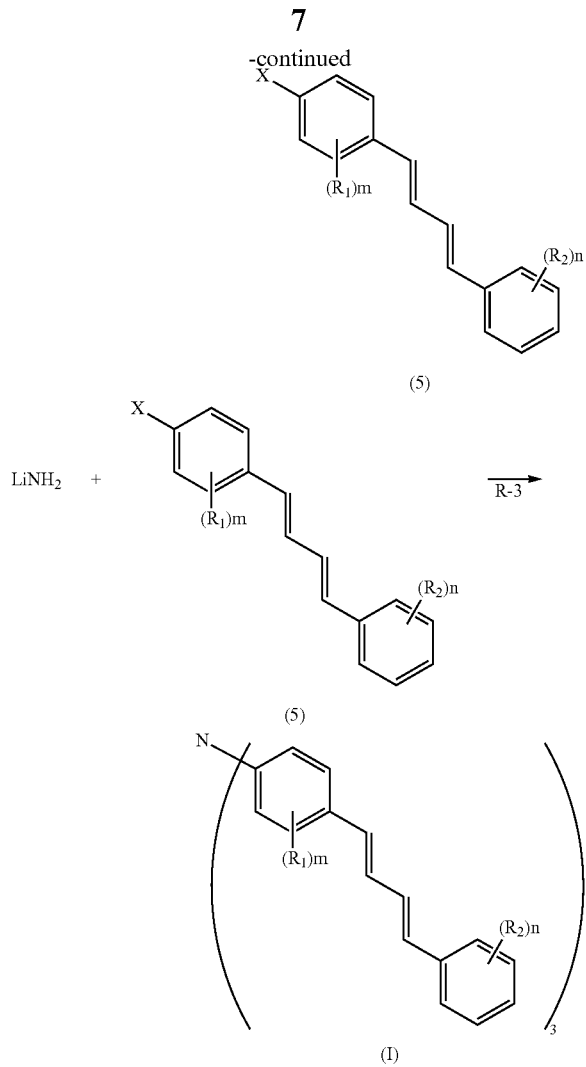

In reaction formulae (R-1) to (R-3), $R_1$, $R_2$, m, and n represent the same as $R_1$, $R_2$, m, and n in general formula (I). X represents a halogen atom.

The following explains the reaction represented by reaction formula (R-1). In reaction formula (R-1), a benzene derivative (1) is caused to react with a compound (2)—that is, triethyl phosphite—to yield a phosphonate derivative (3).

A reaction ratio (benzene derivative (1):triethyl phosphite) of the benzene derivative (1) and triethyl phosphite (i.e., compound (2)) is preferably a molar ratio of 1:1 to 1:2.5. If the number of moles of triethyl phosphite is too small relative to the number of moles of the benzene derivative (1), the percentage yield of the phosphonate derivative (3) may be excessively reduced. On the other hand, if the number of moles of triethyl phosphite is too large relative to the number of moles of the benzene derivative (1), purification of the phosphonate derivative (3) after the reaction may be difficult due to an excessively large amount of triethyl phosphite remaining unreacted.

The reaction of the benzene derivative (1) and triethyl phosphite preferably has a reaction temperature of at least 160° C. and no greater than 200° C., and preferably has a reaction time of at least 2 hours and no greater than 10 hours.

The following explains the reaction represented by reaction formula (R-2). In reaction formula (R-2), the phosphonate derivative (3) is caused to react (Wittig reaction) with a cinnamaldehyde derivative (4) to yield a diphenyl butadiene derivative (5).

A reaction ratio (phosphonate derivative (3):cinnamaldehyde derivative (4)) of the phosphonate derivative (3) and the cinnamaldehyde derivative (4) is preferably a molar ratio of 1:1 to 1:2.5. If the number of moles of the cinnamaldehyde derivative (4) is too small relative to the number of moles of the phosphonate derivative (3), the percentage yield of the diphenyl butadiene derivative (5) may be excessively reduced. If the number of moles of the cinnamaldehyde derivative (4) is too large relative to the number of moles of the phosphonate derivative (3), purification of the diphenyl butadiene derivative (5) may be difficult due to an excessively large amount of the cinnamaldehyde derivative (4) remaining unreacted.

The Wittig reaction may be carried out in the presence of a catalyst. Examples of catalysts that may be used include sodium alkoxides (specifically, sodium methoxide and sodium ethoxide), metal hydrides (specifically, sodium hydride and potassium hydride), and metal salts (specifically, n-butyl lithium). Any one of the catalysts listed above may be used or a combination of any two or more of the catalysts listed above may be used.

The additive amount of a catalyst such as described above is preferably at least 1 mol and no greater than 2 mol relative to 1 mol of the cinnamaldehyde derivative (4). If the additive amount of the catalyst is too small, there may be a significant reduction in reactivity. On the other hand, if the additive amount of the catalyst is too large, the reaction may be difficult to control.

The reaction represented by reaction formula (R-2) may be carried out in a solvent. Examples of solvents that may be used include ethers (specifically, tetrahydrofuran, diethyl ether, and dioxane), halogenated hydrocarbons (specifically, methylene chloride, chloroform, and dichloroethane), and aromatic hydrocarbons (specifically, benzene and toluene).

The reaction of the phosphonate derivative (3) and the cinnamaldehyde derivative (4) preferably has a reaction temperature of at least 0° C. and no greater than 50° C., and preferably has a reaction time of at least 2 hours and no greater than 24 hours.

The following explains the reaction represented by reaction formula (R-3). In the reaction formula (R-3), the resultant diphenyl butadiene derivative (5) is caused to react (coupling reaction) with lithium amide to yield a target compound which is the triarylamine derivative (I).

A reaction ratio (diphenyl butadiene derivative (5):lithium amide) of the diphenyl butadiene derivative (5) and lithium amide is preferably a molar ratio of 5:1 to 1:1.

If the number of moles of lithium amide is too small relative to the number of moles of the diphenyl butadiene derivative (5), the percentage yield of the triarylamine derivative (I) may be excessively reduced. On the other hand, if the number of moles of lithium amide is too large relative to the number of moles of the diphenyl butadiene derivative (5), purification of the triarylamine derivative (I) after the reaction may be difficult due to an excessively large amount of lithium amide remaining unreacted.

The reaction represented by reaction formula (R-3) preferably has a reaction temperature of at least 80° C. and no greater than 140° C., and preferably has a reaction time of at least 2 hours and no greater than 10 hours.

A palladium compound is preferably used as a catalyst in the reaction represented by reaction formula (R-3). By using a palladium compound as a catalyst, the activation energy of the reaction represented by reaction formula (R-3) can be effectively reduced. As a result, the percentage yield of the triarylamine derivative (I) can be improved.

Examples of palladium compounds that can be used include tetravalent palladium compounds, divalent palladium compounds, and other palladium compounds. Specific examples of tetravalent palladium compounds include hexachloro palladium(IV) sodium tetrahydrate and hexachloro palladium(IV) potassium tetrahydrate. Specific examples of divalent palladium compounds include palladium(II) chloride, palladium(II) bromide, palladium(II) acetate, palladium(II) acetylacetate, dichlorobis(benzonitrile)palladium(II), dichlorobis(triphenylphosphine)palladium(II), dichlorotetramine palladium(II), and dichloro(cyclooctа-1,5-diene)palladium(II). Specific examples of other palladium compounds include tris(dibenzylideneacetone)dipalladium(0), tris(dibenzylideneacetone)dipalladium(0) chloroform complex, and tetrakis(triphenylphosphine)palladium(0). Any one of the palladium compounds listed above may be used or a combination of any two or more of the palladium compounds listed above may be used.

The additive amount of the palladium compound is preferably at least 0.0005 mol and no greater than 20 mol relative to 1 mol of the diphenyl butadiene derivative (5), and more preferably at least 0.001 mol and no greater than 1 mol.

A palladium compound such as described above may have a structure including a ligand. As a result, reactivity of the reaction represented by reaction formula (R-3) can be improved. Examples of ligands that can be used include tricyclohexylphosphine, triphenylphosphine, methyldiphenylphosphine, trifurylphosphine, tri(o-tolyl)phosphine, dicyclohexylphenylphosphine, tri(t-butyl)phosphine, 2,2'-bis(diphenylphosphino)-1,1'-binaphthyl, and 2,2'-bis[(diphenylphosphino)diphenyl]ether. Any one of the ligands listed above may be used or a combination of any two or more of the ligands listed above may be used. The additive amount of the ligand is preferably at least 0.0005 mol and no greater than 20 mol relative to 1 mol of the diphenyl butadiene derivative (5), and more preferably at least 0.001 mol and no greater than 1 mol.

The reaction represented by reaction formula (R-3) is preferably carried out in the presence of a base. Through the presence of the base, hydrogen halide produced during the reaction can be quickly neutralized and catalytic activity can be improved. As a result, the percentage yield of the triarylamine derivative (I) can be improved.

The base may be an inorganic base or an organic base. Preferable organic bases for example include alkali metal alkoxides (specifically, sodium methoxide, sodium ethoxide, potassium methoxide, potassium ethoxide, lithium tert-butoxide, sodium tert-butoxide, and potassium tert-butoxide), with sodium tert-butoxide being particularly preferable. Preferable inorganic bases include tripotassium phosphate and cesium fluoride.

In a situation in which at least 0.0005 mol and no greater than 20 mol of the palladium compound is added relative to 1 mol of the diphenyl butadiene derivative (5), the additive amount of the base is preferably at least 1 mol and no greater than 10 mol, and more preferably at least 1 mol and no greater than 5 mol.

The reaction represented by reaction formula (R-3) may be carried out in a solvent. Examples of solvents that may be used include xylene (specifically, o-xylene), toluene, tetrahydrofuran, and dimethyl formamide. Among the above solvents, xylene is preferable.

Second Embodiment

Electrophotographic Photosensitive Member

A second embodiment of the present disclosure is an electrophotographic photosensitive member (also referred to below simply as a photosensitive member). The photosensitive member according to the present embodiment includes a photosensitive layer. The photosensitive layer is either a multi-layer photosensitive layer or a single-layer photosensitive layer.

The photosensitive member according to the present embodiment may be a so-called multi-layer photosensitive member that includes a multi-layer photosensitive layer. The multi-layer photosensitive layer includes at least a charge generating layer and a charge transport layer. The charge transport layer is located on the charge generating layer. The charge generating layer contains at least a charge generating material. The charge transport layer contains at least a hole transport material.

The photosensitive member according to the present embodiment may alternatively be a so-called single-layer photosensitive member that includes a single-layer photosensitive layer. The single-layer photosensitive layer contains at least a charge generating material and a hole transport material in the same layer.

<Multi-Layer Photosensitive Member>

Figure 6A:
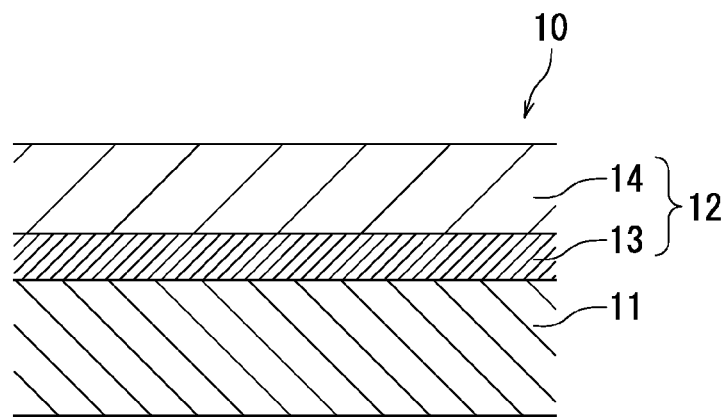
FIGS. 6A and 6B are each a rough cross-sectional illustration of structure of a multi-layer electrophotographic photosensitive member according to an embodiment of the present disclosure.
Figure 6B:
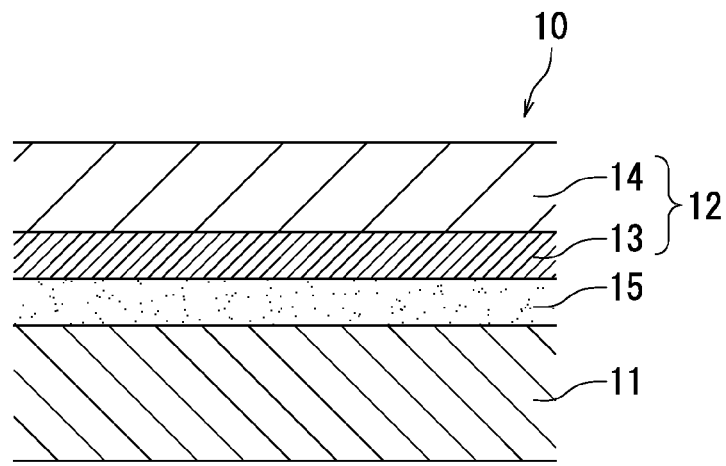

The following explains structure of a multi-layer photosensitive member 10 including a multi-layer photosensitive layer 12 with reference to FIGS. 6A and 6B. As illustrated in FIG. 6A, the multi-layer photosensitive member 10 includes a conductive substrate 11 and the multi-layer photosensitive layer 12. The multi-layer photosensitive layer 12 includes a charge generating layer 13 and a charge transport layer 14 that are stacked on the conductive substrate 11 in stated order. As a result of the charge transport layer 14 being located on the charge generating layer 13, abrasion resistance can be readily improved while also maintaining excellent electrical properties (in particular, sensitivity properties).

The charge generating layer 13 contains a charge generating material. The charge transport layer 14 contains a hole transport material. The charge transport layer 14 may optionally contain a binder resin depending on necessity thereof. The charge transport layer 14 may optionally contain an electron acceptor compound depending on necessity thereof.

No particular limitations are placed on the multi-layer photosensitive member 10 other than including the multi-layer photosensitive layer 12. For example, an intermediate layer 15 may be present between the conductive substrate 11 and the multi-layer photosensitive layer 12 as illustrated in FIG. 6B.

No particular limitations are placed on thickness of the charge generating layer 13 and the charge transport layer 14 so long as the thicknesses thereof are sufficient to enable the charge generating layer 13 and the charge transport layer 14 to implement the respective functions thereof. More specifically, the charge generating layer 13 preferably has a thickness of at least 0.01 μm and no greater than 5 μm, and more preferably at least 0.1 μm and no greater than 3 μm. Also, the charge transport layer 14 preferably has a thickness of at least 2 μm and no greater than 100 μm, and more preferably at least 5 μm and no greater than 50 μm.

<Single-Layer Photosensitive Member>

Figure 7A:
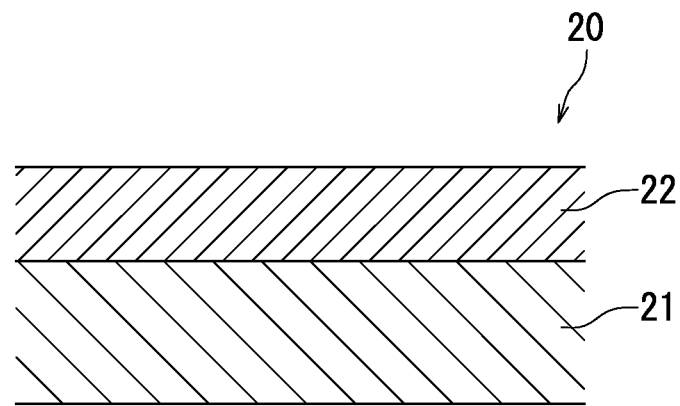
FIGS. 7A and 7B are each a rough cross-sectional illustration of structure of a single-layer electrophotographic photosensitive member according to an embodiment of the present disclosure.
Figure 7B:
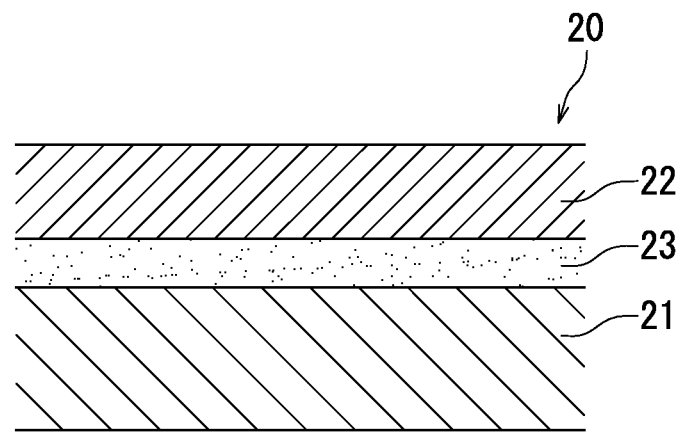

The following explains structure of a single-layer photosensitive member 20 including a single-layer photosensitive layer 22 with reference to FIGS. 7A and 7B. As illustrated in FIG. 7A, the single-layer photosensitive member 20 includes a conductive substrate 21 and the single-layer photosensitive layer 22. The single-layer photosensitive layer 22 is located on the conductive substrate 21. The single-layer photosensitive layer 22 contains a charge generating material and a hole transport material. The single-layer photosensitive layer 22 may optionally contain a binder resin and an electron transport material depending on necessity thereof.

No particular limitations are placed on the single-layer photosensitive member 20 other than including the single-layer photosensitive layer 22. The single-layer photosensitive layer 22 may be located directly on the conductive substrate 21 as illustrated in FIG. 7A. Alternatively, an intermediate layer 23 may be present between the conductive substrate 21 and the single-layer photosensitive layer 22 as illustrated in FIG. 7B.

No particular limitations are placed on thickness of the single-layer photosensitive layer 22 so long as the thickness thereof is sufficient to enable the single-layer photosensitive layer 22 to function as a photosensitive layer. More specifically, the single-layer photosensitive layer 22 preferably has a thickness of at least 5 μm and no greater than 100 μm, and more preferably at least 10 μm and no greater than 50 μm.

In the photosensitive member according to the present embodiment (single-layer photosensitive member 20 or multi-layer photosensitive member 10), the photosensitive layer (single-layer photosensitive layer 22 or multi-layer photosensitive layer 12) is preferably an outermost layer in order to inhibit occurrence of image deletion and restrict production costs. Also, in the multi-layer photosensitive member 10, among the layers of the multi-layer photosensitive layer 12, the charge transport layer 14 is preferably an outermost layer (i.e., a surface layer). Through the above, structure of the single-layer photosensitive member 20 and the multi-layer photosensitive member 10 has been explained with reference to FIGS. 6A, 6B, 7A, and 7B.

<Common Elements>

The following explains elements of configuration that are common to both the single-layer photosensitive member and the multi-layer photosensitive member.

[Conductive Substrate]

In the present embodiment, no particular limitations are placed on the conductive substrate other than at least a surface portion of the conductive substrate being conductive. More specifically, the conductive substrate is formed from a conductive material. Alternatively, the conductive substrate may be formed through coating or vapor deposition of a conductive material on the surface of a plastic material or glass. Examples of conductive materials that can be used include metals such as aluminum, iron, copper, tin, platinum, silver, vanadium, molybdenum, chromium, cadmium, titanium, nickel, palladium, indium, stainless steel, and brass, and alloys of the aforementioned metals. Any one of the conductive materials listed above may be used or a combination of any two or more of the conductive materials listed above may be used.

Among the examples of conductive substrates described above, use of a conductive substrate containing aluminum or aluminum alloy is preferable. The reasoning for the above is that use of such a conductive substrate enables provision of a photosensitive member that tends to have good movement of charge from the photosensitive layer to the conductive substrate and that can be used to form images with better image quality.

No particular limitations are placed on the shape of the conductive substrate which may be selected as appropriate. The conductive substrate may for example be sheet-shaped or drum-shaped. The conductive substrate preferably has sufficient mechanical strength during use.

[Charge Generating Material]

No particular limitations are placed on the charge generating material other than being a charge generating material that can be used in photosensitive members. Examples of charge generating materials that can be used include X-form metal-free phthalocyanine (x-$H_2$Pc), Y-form titanyl phthalocyanine (Y-TiOPc), perylene pigments, bisazo pigments, dithioketopyrrolopyrrole pigments, metal-free naphthalocyanine pigments, metal naphthalocyanine pigments, squaraine pigments, tris-azo pigments, indigo pigments, azulenium pigments, cyanine pigments, powders of inorganic photoconductive materials (for example, selenium, selenium-tellurium, selenium-arsenic, cadmium sulfide, or amorphous silicon), pyrylium salts, anthanthrone-based pigments, triphenylmethane-based pigments, threne pigments, toluidine-based pigments, pyrazoline-based pigments, and quinacridone-based pigments.

Any one charge generating material or a combination of two or more charge generating materials that is absorptive with respect to light in a desired wavelength region may be used. For example, in a digital optical image forming apparatus (for example, a laser beam printer or facsimile machine that uses a light source such as a semiconductor laser), a photosensitive member that is sensitive to a region of wavelengths of at least 700 nm is preferably used. Therefore, a phthalocyanine-based pigment such as X-form metal-free phthalocyanine (x-$H_2$Pc) or Y-form titanyl phthalocyanine (Y-TiOPc) is preferably used. Note that the phthalocyanine-based pigment is not limited to having an X-form or a Y-form crystal structure and phthalocyanine-based pigments having various different crystal structures may be used.

A photosensitive member included in an image forming apparatus that uses a short-wavelength laser light source (for example, a laser light source having an approximate wavelength of at least 350 nm and no greater than 550 nm) preferably contains an anthanthrone-based pigment or a perylene-based pigment as a charge generating material.

The amount of the charge generating material in the multi-layer photosensitive member is preferably at least 5 parts by mass and no greater than 1,000 parts by mass relative to 100 parts by mass of a base resin contained in the charge generating layer, and more preferably at least 30 parts by mass and no greater than 500 parts by mass. Explanation of the base resin is provided further below.

The amount of the charge generating material in the single-layer photosensitive member is preferably at least 0.1 parts by mass and no greater than 50 parts by mass relative to 100 parts by mass of a binder resin contained in the single-layer photosensitive layer, and more preferably at least 0.5 parts by mass and no greater than 30 parts by mass. Explanation of the binder resin is provided further below.

[Charge Transport Material]

In the present embodiment, the photosensitive layer contains a charge transport material. The charge transport material is more specifically a hole transport material.

(Hole Transport Material)

In the present embodiment, the hole transport material contained in the photosensitive member is the triarylamine derivative (I) according to the first embodiment.

The amount of the hole transport material in the multi-layer photosensitive member is preferably at least 10 parts by mass and no greater than 200 parts by mass relative to 100 parts by mass of binder resin, and more preferably at least 20 parts by mass and no greater than 100 parts by mass.

The amount of the hole transport material in the single-layer photosensitive member is preferably at least 10 parts by mass and no greater than 200 parts by mass relative to 100 parts by mass of the binder resin, and more preferably at least 10 parts by mass and no greater than 100 parts by mass.

(Electron Transport Material and Electron Acceptor Compound)

The photosensitive layer may optionally contain an electron transport material or an electron acceptor compound depending on necessity thereof. The single-layer photosensitive layer of the single-layer photosensitive member may contain an electron transport material. Through inclusion of the electron transport material, the single-layer photosensitive layer can transport electrons and the single-layer photosensitive layer can be easily provided with bipolar properties. On the other hand, the multi-layer photosensitive layer of the multi-layer photosensitive member may contain an electron acceptor compound. Inclusion of the electron acceptor compound can improve hole transport by the hole transport material.

Examples of electron transport materials or electron acceptor compounds that can be used include quinone-based compounds (specifically, naphthoquinone-based compounds, diphenoquinone-based compounds, anthraquinone-based compounds, azoquinone-based compounds, nitroanthraquinone-based compounds, and dinitroanthraquinone-based compounds), malononitrile-based compounds, thiopyran-based compounds, trinitrothioxanthone-based compounds, 3,4,5,7-tetranitro-9-fluorenone-based compounds, dinitroanthracene-based compounds, dinitroacridine-based compounds, tetracyanoethylene, 2,4,8-trinitro-thioxanthone, dinitrobenzene, dinitroanthracene, dinitroacridine, succinic anhydride, maleic anhydride, and dibromomaleic anhydride. Any one of the electron transport materials or electron acceptor compounds listed above may be used or a combination of any two or more of the electron transport materials or electron acceptor compounds listed above may be used.

The amount of the electron acceptor compound in the multi-layer photosensitive member is preferably at least 0.1 parts by mass and no greater than 20 parts by mass relative to 100 parts by mass of the binder resin, and more preferably at least 0.5 parts by mass and no greater than 10 parts by mass.

The amount of the electron transport material in the single-layer photosensitive member is preferably at least 5 parts by mass and no greater than 100 parts by mass relative to 100 parts by mass of the binder resin, and more preferably at least 10 parts by mass and no greater than 80 parts by mass.

[Resins]
(Base Resin)

The charge generating layer of the multi-layer photosensitive member contains a charge generating layer binder resin (also referred to as a base resin).

No particular limitations are placed on the base resin other than being a resin that can be used in a charge generating layer of a multi-layer photosensitive member.

The charge generating layer and the charge transport layer of the multi-layer photosensitive member are typically formed in stated order. Therefore, the base resin used in the multi-layer photosensitive member preferably differs from the binder resin in order that the base resin does not dissolve in a solvent of an application liquid used during formation of the charge transport layer.

Specific examples of base resins that can be used include styrene-butadiene copolymers, styrene-acrylonitrile copolymers, styrene-maleate copolymers, acrylic copolymers, styrene-acrylate copolymers, polyethylene resins, ethylene-vinyl acetate copolymers, chlorinated polyethylene resins, polyvinyl chloride resins, polypropylene resins, ionomer resins, vinyl chloride-vinyl acetate copolymers, alkyd resins, polyamide resins, urethane resins, polysulfone resins, diallyl phthalate resins, ketone resins, polyvinyl acetal resins, polyvinyl butyral resins, polyether resins, silicone resins, epoxy resins, phenolic resins, urea resins, melamine resins, epoxy acrylate resins, and urethane-acrylate resins. Use of a polyvinyl butyral resin as the base resin is preferable. Any one of the base resins listed above may be used or a combination of any two or more of the base resins listed above may be used.

(Binder Resin)

The single-layer photosensitive layer of the single-layer photosensitive member or the charge transport layer of the multi-layer photosensitive member may contain a binder resin. Examples of binder resins that can be used include thermoplastic resins (specifically, polycarbonate resins, styrene-based resins, styrene-butadiene copolymers, styrene-acrylonitrile copolymers, styrene-maleate copolymers, styrene-acrylate copolymers, acrylic copolymers, polyethylene resins, ethylene-vinyl acetate copolymers, chlorinated polyethylene resins, polyvinyl chloride resins, polypropylene resins, ionomers, vinyl chloride-vinyl acetate copolymers, alkyd resins, polyamide resins, urethane resins, polyarylate resins, polysulfone resins, diallyl phthalate resins, ketone resins, polyvinyl butyral resins, polyether resins, and polyester resins), thermosetting resins (specifically, silicone resins, epoxy resins, phenolic resins, urea resins, melamine resins, and other crosslinkable thermosetting resins), and photocurable resins (specifically, epoxy acrylate resins and urethane-acrylate copolymers). Among the binder resins listed above, thermoplastic resins are preferable with polycarbonate resins being particularly preferable. Any one of the binder resins listed above may be used or a combination of any two or more of the binder resins listed above may be used.

In terms of molecular weight, the binder resin preferably has a viscosity average molecular weight of at least 40,000, and more preferably at least 40,000 and no greater than 52,500. If the molecular weight of the binder resin is too low, the binder resin may have insufficient abrasion resistance and as a consequence abrasion of the charge transport layer or the single-layer photosensitive layer may have a high tendency to occur. On the other hand, if the molecular weight of the binder resin to too large, formation of the charge transport layer or single-layer photosensitive layer tends to be difficult due to the binder resin having a low tendency to dissolve in a solvent and viscosity of an application liquid being too high during formation of the charge transport layer or the single-layer photosensitive layer.

[Additives]

In the photosensitive member according to the present embodiment, various additives may be contained in one or more of the multi-layer photosensitive layer (specifically, the charge generating layer and the charge transport layer), the single-layer photosensitive layer, and the intermediate layer, so long as such additives do not adversely affect electrophotographic properties of the photosensitive member. Examples of additives that can be used include antidegradants (specifically, antioxidants, radical scavengers, singlet quenchers, and ultraviolet absorbing agents), softeners, surface modifiers, extenders, thickeners, dispersion stabilizers, waxes, acceptors, donors, surfactants, plasticizers, sensitizers, and leveling agents. Specific examples of antioxidants include BHT (di(tert-butyl)p-cresol), hindered phenols, hindered amines, paraphenylenediamine, arylalkanes, hydroquinone, spirochromanes, spiroindanones, derivatives of any of the above compounds, organosulfur compounds, and organophosphorus compounds.

[Intermediate Layer]

The photosensitive member according to the present embodiment may optionally include an intermediate layer (for example, an underlayer). In the single-layer photosensitive member, the intermediate layer is present between the conductive substrate and the single-layer photosensitive layer. In the multi-layer photosensitive member, the intermediate layer is present between the conductive substrate and the charge generating layer. The intermediate layer for example contains inorganic particles and a resin for intermediate layer use (intermediate layer resin). Provision of the intermediate layer may facilitate flow of current generated when the photosensitive member is exposed to light and inhibit increasing resistance, while also maintaining insulation to a sufficient degree so as to inhibit occurrence of leakage current.

Examples of inorganic particles that can be used includes particles of metals (specifically, aluminum, iron, and copper), particles of metal oxides (specifically, titanium oxide, alumina, zirconium oxide, tin oxide, and zinc oxide), and particles of non-metal oxides (specifically, silica). Any one type of inorganic particles listed above may be used or a combination of any two or more types of inorganic particles listed above may be used.

No particular limitations are placed on the intermediate layer resin other than being a resin that can be used to form an intermediate layer.

<Photosensitive Member Production Method>

The following explains a production method for the single-layer photosensitive member. The single-layer photosensitive member is produced by applying an application liquid for single-layer photosensitive layer formation (first application liquid) onto a conductive substrate and drying the first application liquid thereon. The first application liquid is prepared by dissolving or dispersing a charge generating material, a hole transport material, and additive components (for example, a binder resin, an electron transport material, and various additives), depending on necessity thereof, in a solvent.

The following explains a production method for the multi-layer photosensitive member. Specifically, an application liquid for charge generating layer formation (second application liquid) and an application liquid for charge transport layer formation (third application liquid) are first prepared. The second application liquid is applied onto a conductive substrate and dried thereon by an appropriate method to form a charge generating layer. After formation of the charge generating layer, the third application liquid is applied onto the charge generating layer and dried thereon to form a charge transport layer. Through the above process, the multi-layer photosensitive member is produced.

The second application liquid is prepared by dissolving or dispersing a charge generating material and additive components (for example, a base resin and various additives), depending on necessity thereof, in a solvent. The third application liquid is prepared by dissolving or dispersing a hole transport material and additive components (for example, a binder resin, an electron acceptor compound, and various additives), depending on necessity thereof, in a solvent.

No particular limitations are placed on the solvents contained in the application liquids (first application liquid, second application liquid, and third application liquid) other than that the components of each of the application liquids should be soluble or dispersible in the solvent. Specific examples of solvents that can be used include alcohols (for example, methanol, ethanol, isopropanol, and butanol), aliphatic hydrocarbons (for example, n-hexane, octane, and cyclohexane), aromatic hydrocarbons (for example, benzene, toluene, and xylene), halogenated hydrocarbons (for example, dichloromethane, dichloroethane, carbon tetrachloride, and chlorobenzene), ethers (for example, dimethyl ether, diethyl ether, tetrahydrofuran, ethylene glycol dimethyl ether, diethylene glycol dimethyl ether, and propylene glycol monomethyl ether), ketones (for example, acetone, methyl ethyl ketone, and cyclohexanone), esters (for example, ethyl acetate and methyl acetate), dimethyl formaldehyde, dimethyl formamide, and dimethyl sulfoxide. Any one of the solvents listed above may be used or a combination of any two or more of the solvents listed above may be used. In order to improve workability for operators in production of the photosensitive member, a non-halogenated solvent (i.e., a solvent other than a halogenated hydrocarbon) is preferably used.

Each of the application liquids is prepared by mixing the components in order to disperse the components in the solvent. Mixing or dispersion can for example be performed using a bead mill, a roll mill, a ball mill, an attritor, a paint shaker, or an ultrasonic disperser.

The application liquid may for example further contain a surfactant in order to improve dispersibility of the components.

No particular limitations are placed on the method by which the application liquid is applied so long as the method enables uniform application of an application liquid onto a conductive substrate. Examples of application methods that can be used include dip coating, spray coating, spin coating, and bar coating.

No particular limitations are placed on the method by which the application liquid is dried other than being a method for evaporating a solvent contained in an application liquid. The method of drying may for example be heat treatment (hot-air drying) using a high-temperature dryer or a reduced pressure dryer. The heat treatment is for example performed for at least 3 minutes and no greater than 120 minutes at a temperature of at least 40° C. and no greater than 150° C.

Through the above, the photosensitive member according to the present embodiment has been explained. The photosensitive member according to the present embodiment has excellent electrical properties (in particular, sensitivity properties) and excellent surface appearance. A photosensitive member such as described in the present embodiment is thought to enable image formation with high image quality over an extended period of time.

Examples

The following provides more specific explanation of the present disclosure through use of Examples. However, note that the present disclosure is not limited to the scope of the Examples.

(1) Triarylamine Derivative Synthesis

[Synthesis of Triarylamine Derivative (HT-1)]

The triarylamine derivative (HT-1) was synthesized according to the following reaction scheme. Specific explanation of the reaction scheme is provided below.

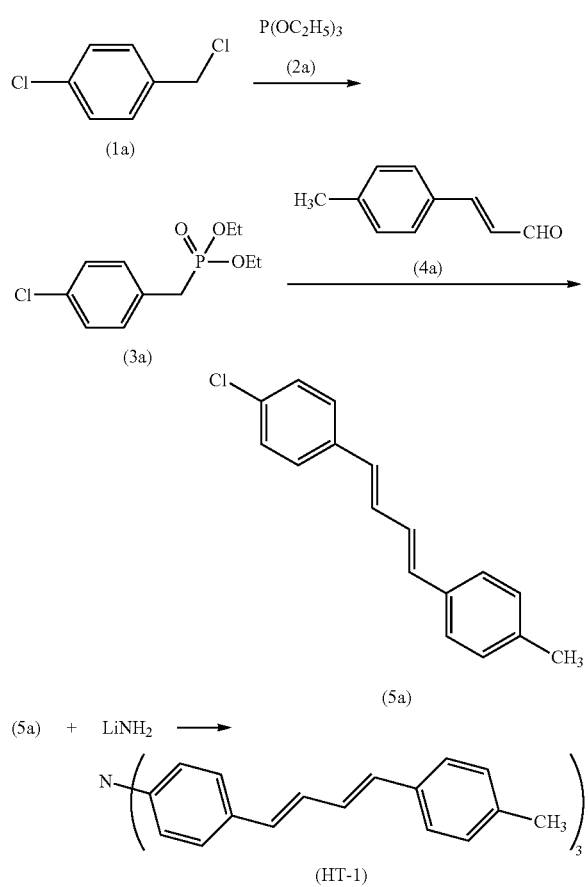

(Synthesis of Compound (3a))

Compound (1a) (16.1 g, 0.1 mol) and compound (2a) (triethyl phosphite, 25 g, 0.15 mol) were added into a flask having a capacity of 200 mL, were stirred for 8 hours at 180° C., and were subsequently cooled to room temperature. Next, excess triethyl phosphite was evaporated under reduced pressure to yield compound (3a) (mass yield 24.1 g, percentage yield 92 mol %) as a white liquid.

(Synthesis of Compound (5a))

The resultant compound (3a) (13 g, 0.05 mol) was added at 0° C. into a two-necked flask having a capacity of 500 mL. Gas in the flask was displaced with argon gas. Next, dried tetrahydrofuran (100 mL) and 28% sodium methoxide (9.3 g, 0.05 mol) were added into the flask and the flask contents were stirred for 30 minutes. After stirring for 30 minutes, compound (4a) (7 g, 0.05 mol) in dried tetrahydrofuran (300 mL) was added into the flask and the flask contents were stirred for 12 hours at room temperature. After pouring the resultant mixture into ion exchanged water, extraction was performed using toluene. A resultant organic layer was washed five times using ion exchanged water. After drying the washed organic layer with anhydrous sodium sulfate, solvent evaporation was performed. The resultant residue was purified using toluene/methanol (20 mL/100 mL) to yield compound (5a) (mass yield 9.8 g, percentage yield 80 mol %) as white crystals.

(Synthesis of Triarylamine Derivative (HT-1))

The resultant compound (5a) (8 g, 0.03 mol), tricyclohexylphosphine (0.0662 g, 0.000189 mol), tris(dibenzylideneacetone)dipalladium(0) (0.0864 g, 0.0000944 mol), sodium tert-butoxide (5.3 g, 0.06 mol), lithium amide (0.24 g, 0.010 mol), and distilled o-xylene (500 mL) were added into a three-necked flask. Gas in the flask was displaced with argon gas. Next, the mixture in the flask was stirred for 5 hours at 120° C. and was subsequently cooled to room temperature. An organic layer of the resultant mixture was washed three times using ion exchanged water. Anhydrous sodium sulfate and activated clay were added to the organic layer in order to perform drying treatment and adsorption treatment. Next, the resultant organic layer was subjected to reduced pressure evaporation in order to remove o-xylene. The resultant residue was purified by column chromatography, using chloroform/hexane (volume ratio 1:1) as a developing solvent, to yield the triarylamine derivative (HT-1) (mass yield 4.5 g, percentage yield 64 mol %).

The triarylamine derivative (HT-1) was measured using a 300 MHz $^1$H-NMR (proton nuclear magnetic resonance) spectrometer. CDCl$_3$ was used as a solvent. The $^1$H-NMR spectrum was used to confirm that the triarylamine derivative (HT-1) had been obtained. FIG. 1 illustrates the $^1$H-NMR spectrum of the triarylamine derivative (HT-1).

[Synthesis of Triarylamine Derivative (HT-2)]

Figure 2:
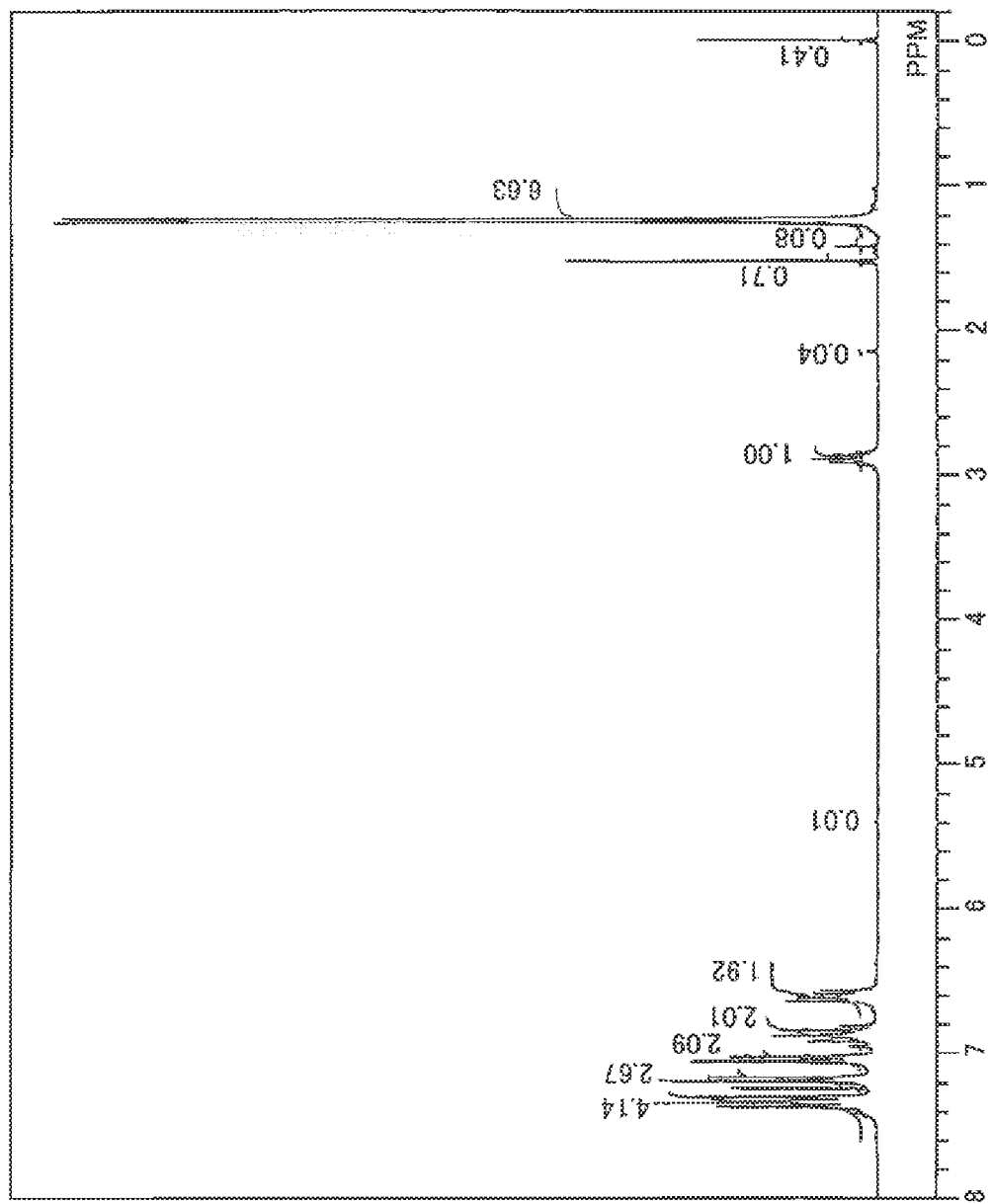
FIG. 2 is a $^1$H-NMR spectrum of a triarylamine derivative represented by formula (HT-2).

Compound (5b) (percentage yield 70 mol %) shown below was synthesized in the same way as the compound (5a) in all aspects other than that compound (4b) shown below was used instead of the compound (4a). Next, the triarylamine derivative (HT-2) (percentage yield 65 mol %) was synthesized in the same way as the triarylamine derivative (HT-1) in all aspects other than that the resultant compound (5b) shown below was used instead of the compound (5a). FIG. 2 illustrates a $^1$H-NMR spectrum (300 MHz, CDCl$_3$ solvent) of the resultant triarylamine derivative (HT-2).

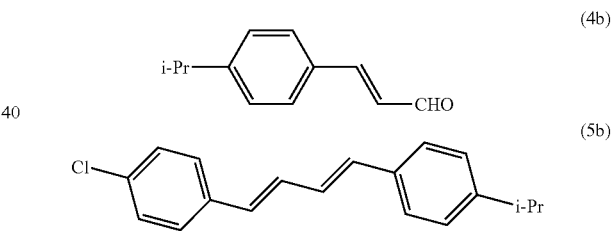

[Synthesis of Triarylamine Derivative (HT-3)]

Figure 3:
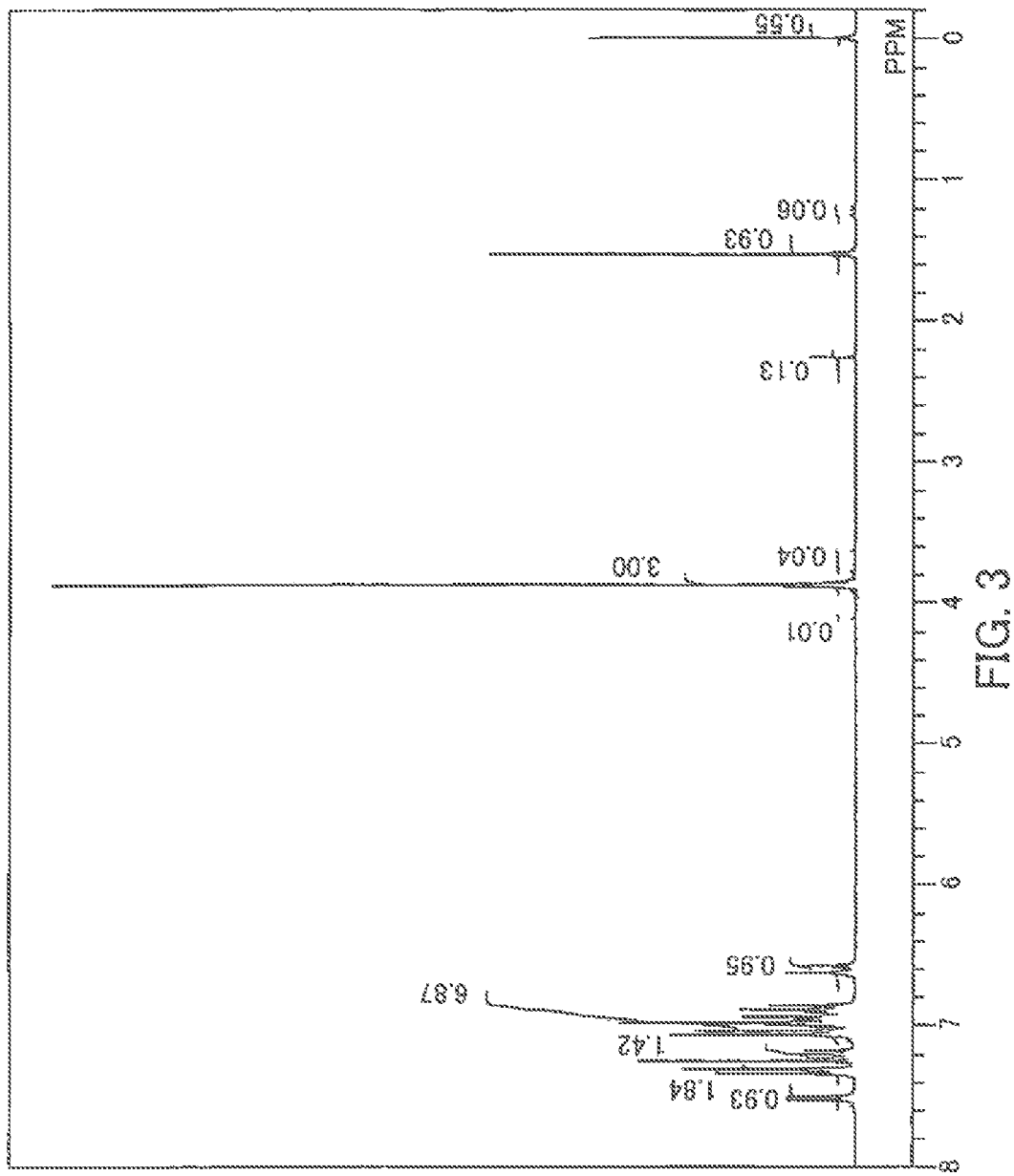
FIG. 3 is a $^1$H-NMR spectrum of a triarylamine derivative represented by formula (HT-3).

Compound (5c) (percentage yield 60 mol %) shown below was synthesized in the same way as the compound (5a) in all aspects other than that compound (4c) shown below was used instead of the compound (4a). Next, the triarylamine derivative (HT-3) (percentage yield 65 mol %) was synthesized in the same way as the triarylamine derivative (HT-1) in all aspects other than that the resultant compound (5c) shown below was used instead of the compound (5a). FIG. 3 illustrates a $^1$H-NMR spectrum (300 MHz, CDCl$_3$ solvent) of the resultant triarylamine derivative (HT-3).

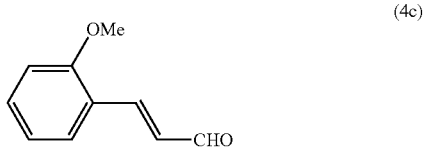

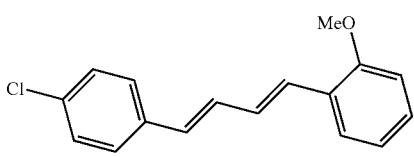
(5c)

[Synthesis of Triarylamine Derivative (HT-4)]

Figure 4:
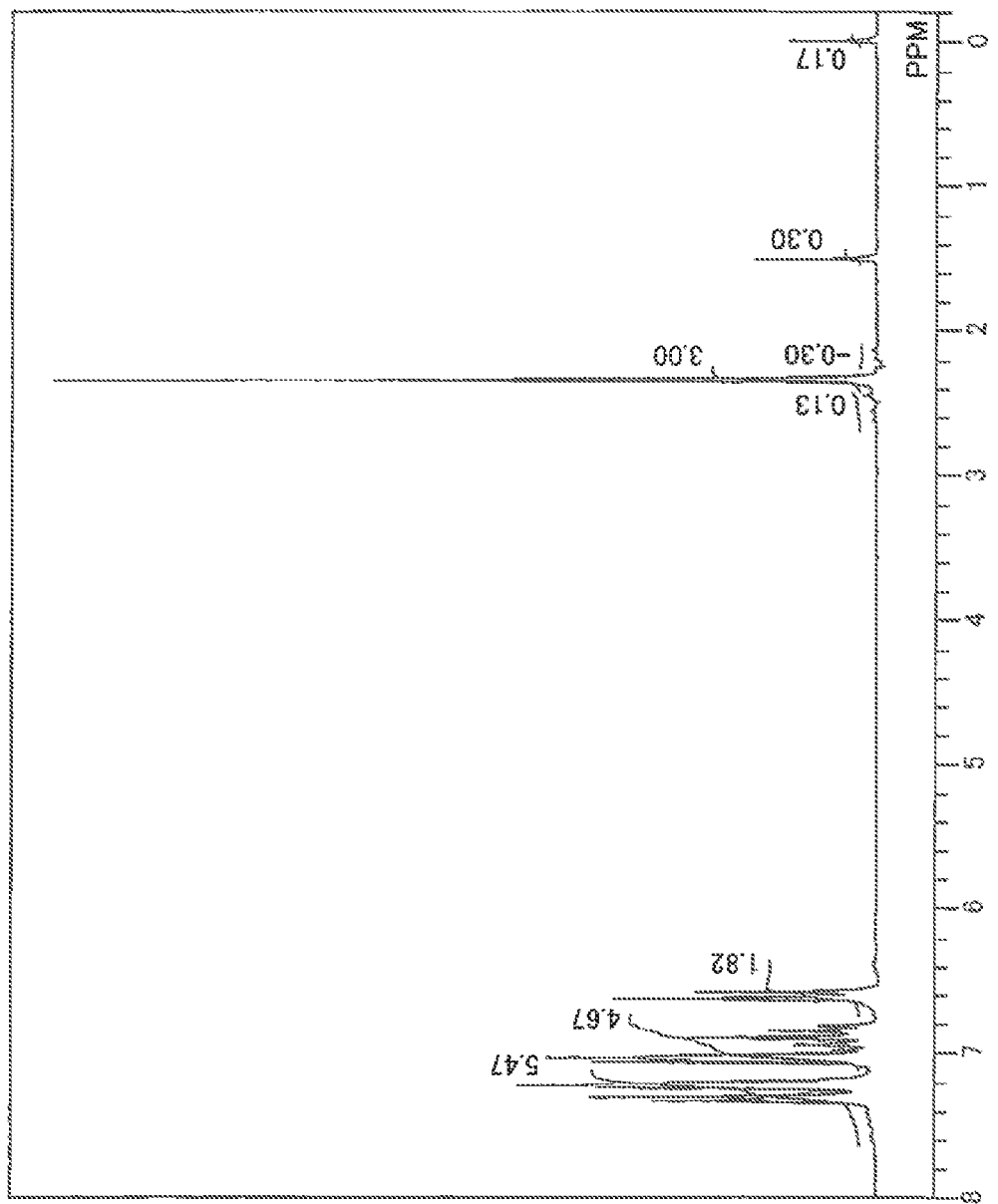
FIG. 4 is a $^1$H-NMR spectrum of a triarylamine derivative represented by formula (HT-4).

Compound (5d) (percentage yield 70 mol %) shown below was synthesized in the same way as the compound (5a) in all aspects other than that compound (4d) shown below was used instead of the compound (4a). Next, the triarylamine derivative (HT-4) (percentage yield 60 mol %) was synthesized in the same way as the triarylamine derivative (HT-1) in all aspects other than that the resultant compound (5d) shown below was used instead of the compound (5a). FIG. 4 illustrates a $^1$H-NMR spectrum (300 MHz, CDCl$_3$ solvent) of the resultant triarylamine derivative (HT-4).

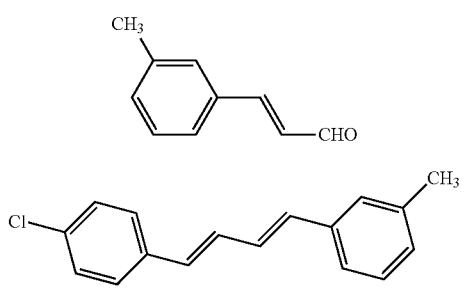
(4d)

(5d)

[Synthesis of Triarylamine Derivative (HT-5)]

Figure 5:
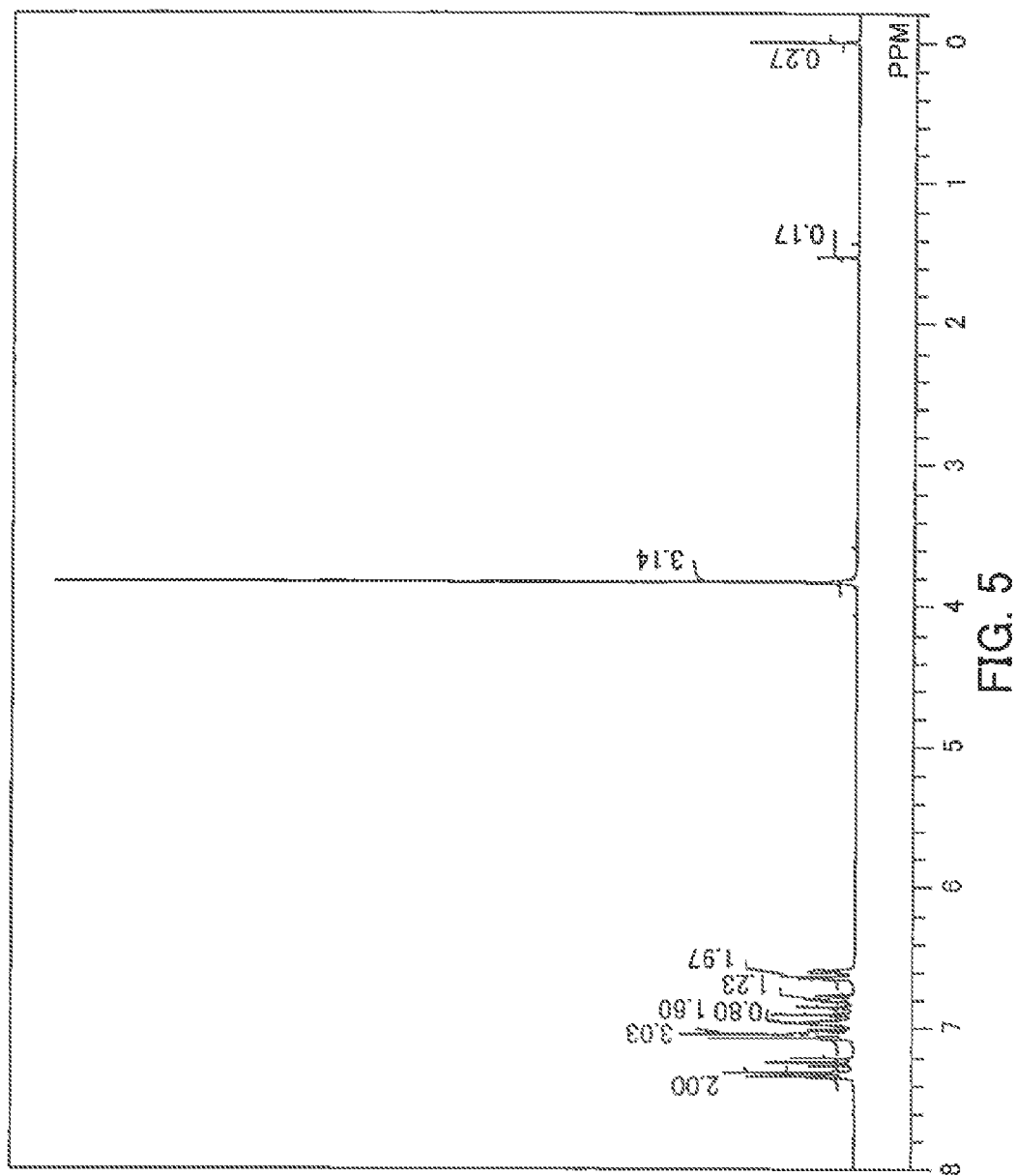
FIG. 5 is a $^1$H-NMR spectrum of a triarylamine derivative represented by formula (HT-5).

Compound (5e) (percentage yield 70 mol %) shown below was synthesized in the same way as the compound (5a) in all aspects other than that compound (4e) shown below was used instead of the compound (4a). Next, the triarylamine derivative (HT-5) (percentage yield 65 mol %) was synthesized in the same way as the triarylamine derivative (HT-1) in all aspects other than that the resultant compound (5e) shown below was used instead of the compound (5a). FIG. 5 illustrates a $^1$H-NMR spectrum (300 MHz, CDCl$_3$ solvent) of the resultant triarylamine derivative (HT-5).

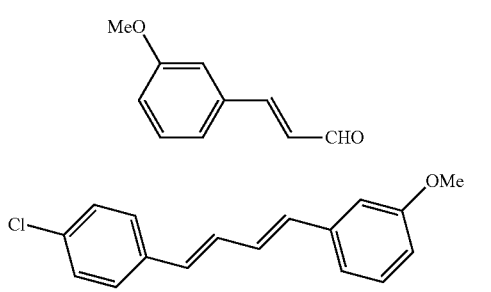
(4e)

(5e)

[Synthesis of Triarylamine Derivative (HT-6)]

Compound (50 (percentage yield 50 mol %) shown below was synthesized in the same way as the compound (5a) in all aspects other than that compound (30 shown below was used instead of the compound (3a) and compound (40 shown below was used instead of the compound (4a). Next, the triarylamine derivative (HT-6) (percentage yield 60 mol %) was synthesized in the same way as the triarylamine derivative (HT-1) in all aspects other than that the resultant compound (50 shown below was used instead of the compound (5a).

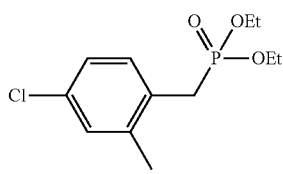
(3f)

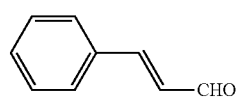
(4f)

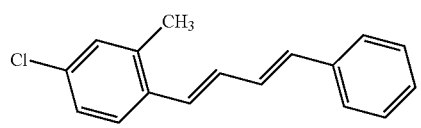
(5f)

[Synthesis of Triarylamine Derivative (HT-7)]

Compound (5g) (percentage yield 70 mol %) shown below was synthesized in the same way as the compound (5a) in all aspects other than that compound (4g) shown below was used instead of the compound (4a). Next, the triarylamine derivative (HT-7) (percentage yield 65 mol %) was synthesized in the same way as the triarylamine derivative (HT-1) in all aspects other than that the resultant compound (5g) shown below was used instead of the compound (5a).

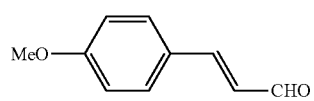
(4g)

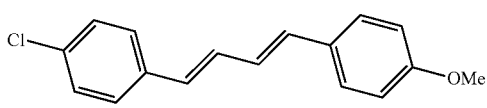
(5g)

(2) Multi-Layer Photosensitive Member Production

[Photosensitive Member (A-1)]

The following explains production of photosensitive member (A-1) which is a multi-layer photosensitive member.

(Intermediate Layer Formation)

First, surface treated titanium oxide (test sample SMT-02 produced by Tayca Corporation, number average primary particle size 10 nm) was prepared. The surface treated titanium oxide was titanium oxide prepared as described below. Titanium oxide was surface treated using alumina and silica. After being subjected to the above surface treatment, the titanium oxide was further surface treated using methyl hydrogen polysiloxane during wet dispersion.

Next, an application liquid for intermediate layer formation was prepared. More specifically, the surface treated titanium oxide (2.8 parts by mass) and copolyamide resin (DAIAMID X4685 produced by Daicel-Evonik Ltd.) (1 part by mass) were added to a solvent including ethanol (10 parts by mass) and butanol (2 parts by mass). Next, mixing was performed for 5 hours using a bead mill in order to disperse the materials in the solvent and thereby prepare the application liquid for intermediate layer formation.

Next, the resultant application liquid for intermediate layer formation was filtered using a filter having a pore size of 5 μm. After filtration, the application liquid for intermediate layer formation was applied onto a conductive substrate—an aluminum drum-shaped support (diameter 30 mm, total length 238.5 mm)—by dip coating. Next, the applied application liquid was dried for 30 minutes at 130° C., thereby forming an intermediate layer (film thickness 1.5 μm) on the conductive substrate (drum-shaped support).

(Charge Generating Layer Formation)

Y-form titanyl phthalocyanine (1 part by mass) as a charge generating material and polyvinyl butyral resin (Denka Butyral 6000EP produced by Denki Kagaku Kogyo Kabushiki Kaisha) (1 part by mass) as a base resin were added to a solvent including propylene glycol monomethyl ether (40 parts by mass) and tetrahydrofuran (40 parts by mass). Next, mixing was performed for 2 hours using a bead mill in order to disperse the materials in the solvent and thereby obtain the second application liquid. Next, the obtained second application liquid was filtered using a filter having a pore size of 3 μm. After filtration, the resultant filtrate was applied by dip coating onto the intermediate layer formed as described above and was dried for 5 minutes at 50° C. Through the above process, a charge generating layer (film thickness 0.3 μm) was formed on the intermediate layer.

(Charge Transport Layer Formation)

The triarylamine derivative (HT-1) (70 parts by mass) as a hole transport material, BHT (di(tert-butyl)p-cresol) (5 parts by mass) as an antioxidant, and Z-form polycarbonate resin (Panlite (registered Japanese trademark) TS-2050 produced by Teijin Limited, viscosity average molecular weight 50,200) (100 parts by mass) as a binder resin were added to a solvent including tetrahydrofuran (430 parts by mass) and toluene (430 parts by mass). Next, mixing was performed for 12 hours using a circulating ultrasonic disperser in order to disperse the components in the solvent and thereby obtain the third application liquid.

The third application liquid was applied through the same operation as the second application liquid onto the charge generating layer formed as described above. Next, the third application liquid was dried for 30 minutes at 130° C. to yield a charge transport layer (film thickness 20 μm) on the charge generating layer. The photosensitive member A-1 (multi-layer photosensitive member) was obtained as a result of the process described above. In the photosensitive member (A-1), the intermediate layer, the charge generating layer, and the charge transport layer were stacked in stated order on the conductive substrate.

[Photosensitive Member (A-2)]

A photosensitive member (A-2) was produced according to the same method as the photosensitive member (A-1) in all aspects other than that the triarylamine derivative (HT-2) was used as the hole transport material instead of the triarylamine derivative (HT-1).

[Photosensitive Member (A-3)]

A photosensitive member (A-3) was produced according to the same method as the photosensitive member (A-1) in all aspects other than that the triarylamine derivative (HT-3) was used as the hole transport material instead of the triarylamine derivative (HT-1).

[Photosensitive Member (A-4)]

A photosensitive member (A-4) was produced according to the same method as the photosensitive member (A-1) in all aspects other than that the triarylamine derivative (HT-4) was used as the hole transport material instead of the triarylamine derivative (HT-1).

[Photosensitive Member (A-5)]

A photosensitive member (A-5) was produced according to the same method as the photosensitive member (A-1) in all aspects other than that the triarylamine derivative (HT-5) was used as the hole transport material instead of the triarylamine derivative (HT-1).

[Photosensitive Member (A-6)]

A photosensitive member (A-6) was produced according to the same method as the photosensitive member (A-1) in all aspects other than that the triarylamine derivative (HT-6) was used as the hole transport material instead of the triarylamine derivative (HT-1).

[Photosensitive Member (A-7)]

A photosensitive member (A-7) was produced according to the same method as the photosensitive member (A-1) in all aspects other than that the triarylamine derivative (HT-7) was used as the hole transport material instead of the triarylamine derivative (HT-1).

[Photosensitive Member (B-1)]

A photosensitive member (B-1) was produced according to the same method as the photosensitive member (A-1) in all aspects other than that a triarylamine derivative (HT-A) shown below was used as the hole transport material instead of the triarylamine derivative (HT-1).

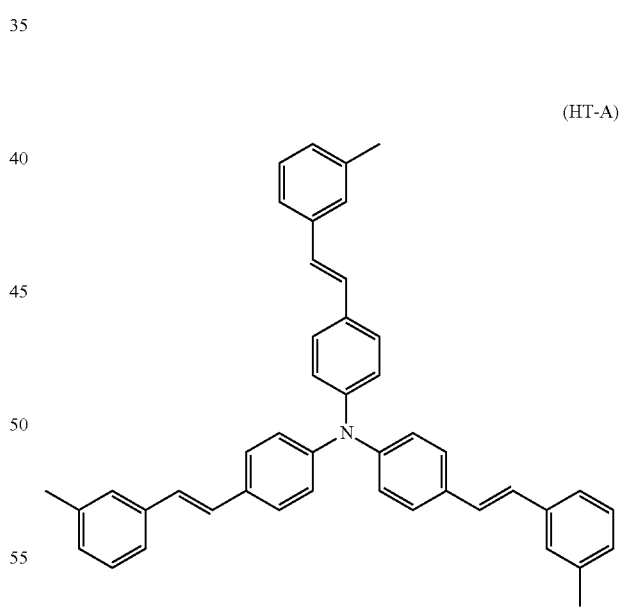

(HT-A)

[Photosensitive Member (B-2)]

A photosensitive member (B-2) was produced according to the same method as the photosensitive member (A-1) in all aspects other than that a triarylamine derivative (HT-B) shown below was used as the hole transport material instead of the triarylamine derivative (HT-1).

(HT-B)

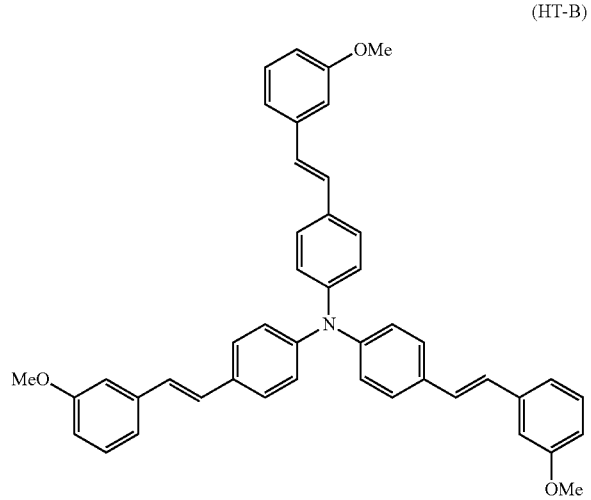 [SMILES: COc1cccc(/C=C/c2ccc(N(c3ccc(/C=C/c4cccc(OC)c4)cc3)c3ccc(/C=C/c4cccc(OC)c4)cc3)cc2)c1]

(3) Single-Layer Photosensitive Member Production

[Photosensitive Member (C-1)]

X-form metal-free phthalocyanine (5 parts by mass) as a charge generating material, the triarylamine derivative (HT-1) (80 parts by mass) as a hole transport material, a compound (ET-1) (50 parts by mass) shown below as an electron transport material, Z-form polycarbonate resin (Panlite (registered Japanese trademark) TS-2050 produced by Teijin Limited, viscosity average molecular weight 50,200) (100 parts by mass) as a binder resin, and tetrahydrofuran (800 parts by mass) as a solvent were added into a container. The container contents were mixed for 50 hours using a ball mill in order to disperse the materials in the solvent and thereby obtain an application liquid for single-layer photosensitive layer formation (first application liquid).

(ET-1)

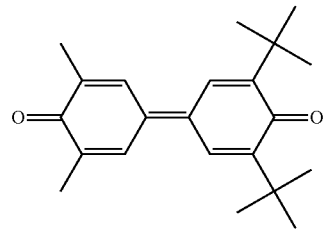

Next, the obtained first application liquid was applied onto a conductive substrate—an aluminum drum-shaped support (diameter 30 mm, total length 238.5 mm)—by dip coating. Heat treatment (hot-air drying) was subsequently performed for 30 minutes at 100° C. to form a single-layer photosensitive layer (film thickness 25 μm). A photosensitive member (C-1) (single-layer photosensitive member) was obtained as a result of the above process.

[Photosensitive Member (C-2)]

A photosensitive member (C-2) was produced according to the same method as the photosensitive member (C-1) in all aspects other than that a compound (ET-4) shown below was used as the electron transport material instead of the compound (ET-1).

(ET-4)

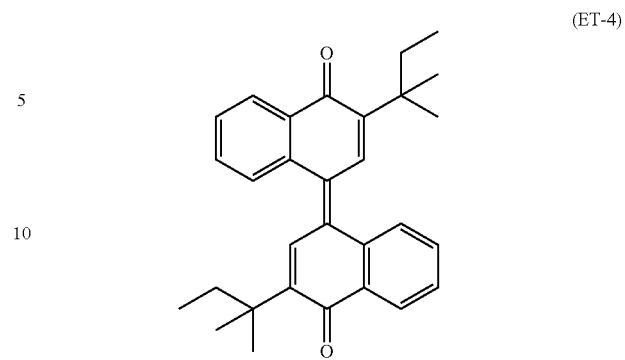

[Photosensitive Member (C-3)]

A photosensitive member (C-3) was produced according to the same method as the photosensitive member (C-1) in all aspects other than that Y-form titanyl phthalocyanine was used as the charge generating material instead of X-form metal-free phthalocyanine and the compound (ET-4) was used as the electron transport material instead of the compound (ET-1).

[Photosensitive Member (C-4)]

A photosensitive member (C-4) was produced according to the same method as the photosensitive member (C-1) in all aspects other than that the triarylamine derivative (HT-2) was used as the hole transport material instead of the triarylamine derivative (HT-1).

[Photosensitive Member (C-5)]

A photosensitive member (C-5) was produced according to the same method as the photosensitive member (C-1) in all aspects other than that the triarylamine derivative (HT-2) was used as the hole transport material instead of the triarylamine derivative (HT-1) and the compound (ET-4) was used as the electron transport material instead of the compound (ET-1).

[Photosensitive Member (C-6)]

A photosensitive member (C-6) was produced according to the same method as the photosensitive member (C-1) in all aspects other than the changes described below. Y-form titanyl phthalocyanine was used as the charge generating material instead of X-form metal-free phthalocyanine. The triarylamine derivative (HT-2) was used as the hole transport material instead of the triarylamine derivative (HT-1). The compound (ET-4) was used as the electron transport material instead of the compound (ET-1).

[Photosensitive Member (C-7)]

A photosensitive member (C-7) was produced according to the same method as the photosensitive member (C-1) in all aspects other than that the triarylamine derivative (HT-3) was used as the hole transport material instead of the triarylamine derivative (HT-1).

[Photosensitive Member (C-8)]

A photosensitive member (C-8) was produced according to the same method as the photosensitive member (C-1) in all aspects other than that the triarylamine derivative (HT-3) was used as the hole transport material instead of the triarylamine derivative (HT-1) and the compound (ET-4) was used as the electron transport material instead of the compound (ET-1).

[Photosensitive Member (C-9)]

A photosensitive member (C-9) was produced according to the same method as the photosensitive member (C-1) in all aspects other than the changes described below. Y-form titanyl phthalocyanine was used as the charge generating material instead of X-form metal-free phthalocyanine. The triarylamine derivative (HT-3) was used as the hole transport material instead of the triarylamine derivative (HT-1). The compound (ET-4) was used as the electron transport material instead of the compound (ET-1).

[Photosensitive Member (C-10)]

A photosensitive member (C-10) was produced according to the same method as the photosensitive member (C-1) in all aspects other than that the triarylamine derivative (HT-4) was used as the hole transport material instead of the triarylamine derivative (HT-1).

[Photosensitive Member (C-11)]

A photosensitive member (C-11) was produced according to the same method as the photosensitive member (C-1) in all aspects other than that the triarylamine derivative (HT-4) was used as the hole transport material instead of the triarylamine derivative (HT-1) and the compound (ET-4) was used as the electron transport material instead of the compound (ET-1).

[Photosensitive Member (C-12)]

A photosensitive member (C-12) was produced according to the same method as the photosensitive member (C-1) in all aspects other than the changes described below. Y-form titanyl phthalocyanine was used as the charge generating material instead of X-form metal-free phthalocyanine. The triarylamine derivative (HT-4) was used as the hole transport material instead of the triarylamine derivative (HT-1). The compound (ET-4) was used as the electron transport material instead of the compound (ET-1).

[Photosensitive Member (C-13)]

A photosensitive member (C-13) was produced according to the same method as the photosensitive member (C-1) in all aspects other than that the triarylamine derivative (HT-5) was used as the hole transport material instead of the triarylamine derivative (HT-1).

[Photosensitive Member (C-14)]

A photosensitive member (C-14) was produced according to the same method as the photosensitive member (C-1) in all aspects other than that the triarylamine derivative (HT-5) was used as the hole transport material instead of the triarylamine derivative (HT-1) and the compound (ET-4) was used as the electron transport material instead of the compound (ET-1).

[Photosensitive Member (C-15)]

A photosensitive member (C-15) was produced according to the same method as the photosensitive member (C-1) in all aspects other than the changes described below. Y-form titanyl phthalocyanine was used as the charge generating material instead of X-form metal-free phthalocyanine. The triarylamine derivative (HT-5) was used as the hole transport material instead of the triarylamine derivative (HT-1). The compound (ET-4) was used as the electron transport material instead of the compound (ET-1).

[Photosensitive Member (C-16)]

A photosensitive member (C-16) was produced according to the same method as the photosensitive member (C-1) in all aspects other than that the triarylamine derivative (HT-6) was used as the hole transport material instead of the triarylamine derivative (HT-1).

[Photosensitive Member (C-17)]

A photosensitive member (C-17) was produced according to the same method as the photosensitive member (C-1) in all aspects other than that the triarylamine derivative (HT-6) was used as the hole transport material instead of the triarylamine derivative (HT-1) and the compound (ET-4) was used as the electron transport material instead of the compound (ET-1).

[Photosensitive Member (C-18)]

A photosensitive member (C-18) was produced according to the same method as the photosensitive member (C-1) in all aspects other than the changes described below. Y-form titanyl phthalocyanine was used as the charge generating material instead of X-form metal-free phthalocyanine. The triarylamine derivative (HT-6) was used as the hole transport material instead of the triarylamine derivative (HT-1). The compound (ET-4) was used as the electron transport material instead of the compound (ET-1).

[Photosensitive Member (C-19)]

A photosensitive member (C-19) was produced according to the same method as the photosensitive member (C-1) in all aspects other than that the triarylamine derivative (HT-7) was used as the hole transport material instead of the triarylamine derivative (HT-1).

[Photosensitive Member (C-20)]

A photosensitive member (C-20) was produced according to the same method as the photosensitive member (C-1) in all aspects other than that the triarylamine derivative (HT-7) was used as the hole transport material instead of the triarylamine derivative (HT-1) and the compound (ET-4) was used as the electron transport material instead of the compound (ET-1).

[Photosensitive Member (C-21)]

A photosensitive member (C-21) was produced according to the same method as the photosensitive member (C-1) in all aspects other than the changes described below. Y-form titanyl phthalocyanine was used as the charge generating material instead of X-form metal-free phthalocyanine. The triarylamine derivative (HT-7) was used as the hole transport material instead of the triarylamine derivative (HT-1). The compound (ET-4) was used as the electron transport material instead of the compound (ET-1).

[Photosensitive Member (D-1)]

A photosensitive member (D-1) was produced according to the same method as the photosensitive member (C-1) in all aspects other than that the triarylamine derivative (HT-A) was used as the hole transport material instead of the triarylamine derivative (HT-1).

[Photosensitive Member (D-2)]

A photosensitive member (D-2) was produced according to the same method as the photosensitive member (C-1) in all aspects other than that the triarylamine derivative (HT-A) was used as the hole transport material instead of the triarylamine derivative (HT-1) and the compound (ET-4) was used as the electron transport material instead of the compound (ET-1). [Photosensitive Member (D-3)]

A photosensitive member (D-3) was produced according to the same method as the photosensitive member (C-1) in all aspects other than the changes described below. Y-form titanyl phthalocyanine was used as the charge generating material instead of X-form metal-free phthalocyanine. The triarylamine derivative (HT-A) was used as the hole transport material instead of the triarylamine derivative (HT-1). The compound (ET-4) was used as the electron transport material instead of the compound (ET-1).

[Photosensitive Member (D-4)]

A photosensitive member (D-4) was produced according to the same method as the photosensitive member (C-1) in all aspects other than that the triarylamine derivative (HT-B) was used as the hole transport material instead of the triarylamine derivative (HT-1).

[Photosensitive Member (D-5)]

A photosensitive member (D-5) was produced according to the same method as the photosensitive member (C-1) in all aspects other than that the triarylamine derivative (HT-B)

was used as the hole transport material instead of the triarylamine derivative (HT-1) and the compound (ET-4) was used as the electron transport material instead of the compound (ET-1).

[Photosensitive Member (D-6)]

A photosensitive member (D-6) was produced according to the same method as the photosensitive member (C-1) in all aspects other than the changes described below. Y-form titanyl phthalocyanine was used as the charge generating material instead of X-form metal-free phthalocyanine. The triarylamine derivative (HT-B) was used as the hole transport material instead of the triarylamine derivative (HT-1). The compound (ET-4) was used as the electron transport material instead of the compound (ET-1).

The photosensitive members produced as described above were each evaluated as follows.

(4) Evaluation of Multi-Layer Photosensitive Member Electrical Properties

With respect to each of the multi-layer photosensitive members (A-1) to (A-7) and (B-1) to (B-2), the multi-layer photosensitive member was charged to a negative polarity at a rotation rate of 31 rpm using a drum sensitivity test device (product of Gen-Tech, Inc.). The surface potential of the multi-layer photosensitive member was measured after charging. The measured surface potential was taken to be an initial surface potential ($V_0$, units: −V). Next, monochromatic light (wavelength 780 nm, half-width 20 nm, light intensity 0.4 µJ/cm$^2$) was isolated from light emitted by a halogen lamp using a band pass filter. The isolated monochromatic light was irradiated onto the surface of the multi-layer photosensitive member (irradiation time 1.5 seconds). The surface potential of the multi-layer photosensitive member was measured once 0.5 seconds had elapsed after completion of the irradiation. The measured surface potential was taken to be a residual potential ($V_L$, units: −V). Measurement was performed under ambient conditions of 23° C. and 50% relative humidity.

(5) Evaluation of Single-Layer Photosensitive Member Electrical Properties

With respect to each of the single-layer photosensitive members (C-1) to (C-21) and (D-1) to (D-6), the single-layer photosensitive member was charged to a positive polarity using the drum sensitivity test device (product of Gen-Tech, Inc.). The surface potential of the single-layer photosensitive member was measured after charging. The measured surface potential was taken to be an initial surface potential ($V_0$, units: +V). Next, monochromatic light (wavelength 780 nm, half-width 20 nm, light intensity 1.5 µJ/cm$^2$) was isolated from light emitted by a halogen lamp using a band pass filter. The isolated monochromatic light was irradiated onto the surface of the single-layer photosensitive member (irradiation time 1.5 seconds). The surface potential of the single-layer photosensitive member was measured once 0.5 seconds had elapsed after completion of the irradiation. The measured surface potential was taken to be a residual potential ($V_L$, units: +V). Measurement was performed under ambient conditions of 23° C. and 50% relative humidity.

(6) Evaluation of Photosensitive Member External Appearance

With respect to each of the photosensitive members (A-1) to (A-7), (B-1) to (B-2), (C-1) to (C-21), and (D-1) to (D-6), the photosensitive member was observed under an optical microscope at a magnification of ×50. Through the above observation it was confirmed whether or not a crystallized portion was present at the surface of the photosensitive member. Based on the result of the above confirmation, the external appearance of the photosensitive member was evaluated in accordance with the following standard.

Good: No crystallized portion observed
Poor: Crystallized portion observed

Table 1 shows the hole transport material contained in the charge transport layer and the various evaluation results for each of the multi-layer photosensitive members (A-1) to (A-7) and (B-1) to (B-2). Table 2 shows the charge generating material, the hole transport material, and the electron transport material contained in the single-layer photosensitive layer and the various evaluation results for each of the single-layer photosensitive members (C-1) to (C-21) and (D-1) to (D-6).

TABLE 1

| Multi-layer photosensitive member | Hole transport material | Electrical properties $V_0$ [−V] | $V_L$ [−V] | Evaluation of external appearance (presence of crystallization) |
|---|---|---|---|---|
| A-1 | HT-1 | 700 | 87 | Good |
| A-2 | HT-2 | 700 | 85 | Good |
| A-3 | HT-3 | 700 | 88 | Good |
| A-4 | HT-4 | 700 | 87 | Good |
| A-5 | HT-5 | 700 | 91 | Good |
| A-6 | HT-6 | 700 | 104 | Good |
| A-7 | HT-7 | 700 | 90 | Good |
| B-1 | HT-A | 700 | 125 | Poor |
| B-2 | HT-B | 700 | 123 | Poor |

TABLE 2

| Single-layer photosensitive material | Charge generating material | Hole transport member | Electron transport material | Electrical properties $V_0$ [+V] | $V_L$ [+V] | Evaluation of external appearance (presence of crystallization) |
|---|---|---|---|---|---|---|
| C-1 | X-form metal-free phthalocyanine | HT-1 | ET-1 | 698 | 97 | Good |
| C-2 | X-form metal-free phthalocyanine | HT-1 | ET-4 | 700 | 98 | Good |
| C-3 | Y-form titanyl phthalocyanine | HT-1 | ET-4 | 700 | 93 | Good |
| C-4 | X-form metal-free phthalocyanine | HT-2 | ET-1 | 700 | 97 | Good |
| C-5 | X-form metal-free phthalocyanine | HT-2 | ET-4 | 699 | 99 | Good |
| C-6 | Y-form titanyl phthalocyanine | HT-2 | ET-4 | 699 | 94 | Good |
| C-7 | X-form metal-free phthalocyanine | HT-3 | ET-1 | 700 | 99 | Good |
| C-8 | X-form metal-free phthalocyanine | HT-3 | ET-4 | 699 | 98 | Good |
| C-9 | Y-form titanyl phthalocyanine | HT-3 | ET-4 | 699 | 94 | Good |
| C-10 | X-form metal-free phthalocyanine | HT-4 | ET-1 | 700 | 103 | Good |
| C-11 | X-form metal-free phthalocyanine | HT-4 | ET-4 | 699 | 103 | Good |
| C-12 | Y-form titanyl phthalocyanine | HT-4 | ET-4 | 700 | 99 | Good |

TABLE 2-continued

| Single-layer photosensitive material | Charge generating material | Hole transport member | Electron transport material | Electrical properties $V_O$ [+V] | $V_L$ [+V] | Evaluation of external appearance (presence of crystallization) |
|---|---|---|---|---|---|---|
| C-13 | X-form metal-free phthalocyanine | HT-5 | ET-1 | 700 | 98 | Good |
| C-14 | X-form metal-free phthalocyanine | HT-5 | ET-4 | 699 | 100 | Good |
| C-15 | Y-form titanyl phthalocyanine | HT-5 | ET-4 | 700 | 95 | Good |
| C-16 | X-form metal-free phthalocyanine | HT-6 | ET-1 | 700 | 104 | Good |
| C-17 | X-form metal-free phthalocyanine | HT-6 | ET-4 | 699 | 106 | Good |
| C-18 | Y-form titanyl phthalocyanine | HT-6 | ET-4 | 700 | 100 | Good |
| C-19 | X-form metal-free phthalocyanine | HT-7 | ET-1 | 700 | 99 | Good |
| C-20 | X-form metal-free phthalocyanine | HT-7 | ET-4 | 699 | 98 | Good |
| C-21 | Y-form titanyl phthalocyanine | HT-7 | ET-4 | 699 | 94 | Good |
| D-1 | X-form metal-free phthalocyanine | HT-A | ET-1 | 699 | 125 | Poor |
| D-2 | X-form metal-free phthalocyanine | HT-A | ET-4 | 700 | 122 | Poor |
| D-3 | Y-form titanyl phthalocyanine | HT-A | ET-4 | 701 | 119 | Poor |
| D-4 | X-form metal-free phthalocyanine | HT-B | ET-1 | 699 | 125 | Poor |
| D-5 | X-form metal-free phthalocyanine | HT-B | ET-4 | 700 | 122 | Poor |
| D-6 | Y-form titanyl phthalocyanine | HT-B | ET-4 | 701 | 119 | Poor |

With respect to the photosensitive members (A-1) to (A-7) and (C-1) to (C-21) in which the triarylamine derivatives (HT-1) to (HT-7) were used, as is clear from Tables 1 and 2, not only was crystallization inhibited in the photosensitive layer, but also an absolute value of residual potential measured in evaluation of electrical properties tended to be small. Therefore, a photosensitive member having excellent electrical properties while also maintaining excellent surface appearance can be obtained through inclusion of any of the triarylamine derivatives (HT-1) to (HT-7) in the photosensitive member as a hole transport material.

What is claimed is:

1. A triarylamine derivative represented by general formula (I)

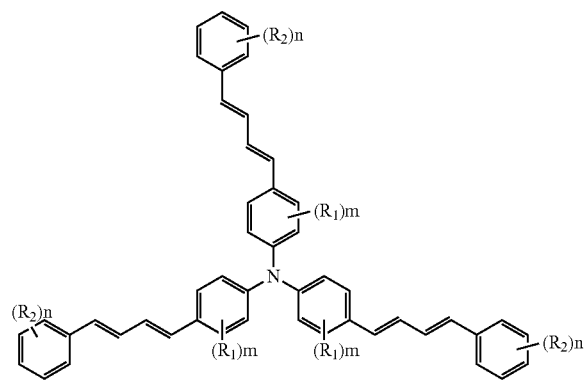

(I)

where, in the general formula (I), $R_1$ and $R_2$ each represent, independently of one another, a chemical group selected from the group consisting of a halogen atom, an optionally substituted alkyl group having a carbon number of at least 1 and no greater than 6, an optionally substituted alkoxy group having a carbon number of at least 1 and no greater than 6, and an optionally substituted aryl group having a carbon number of at least 6 and no greater than 12, m and n each represent an integer of at least 0 and no greater than 4, when m represents an integer greater than 1, chemical groups $R_1$ bonded to the same aromatic ring may be the same or different to one another, and when n represents an integer greater than 1, chemical groups $R_2$ bonded to the same aromatic ring may be the same or different to one another.

2. The triarylamine derivative according to claim 1, wherein in the general formula (I), $R_1$ and $R_2$ each represent, independently of one another, a chemical group selected from the group consisting of an alkyl group having a carbon number of at least 1 and no greater than 6 and an alkoxy group having a carbon number of at least 1 and no greater than 6, and m and n each represent 0 or 1.

3. The triarylamine derivative according to claim 1, wherein in the general formula (I), n represents 1, and $R_2$ is located at an ortho or para position relative to a butadienyl group.

4. The triarylamine derivative according to claim 1 represented by any one of formulae (HT-1), (HT-2), (HT-3), (HT-4), (HT-5), (HT-6), and (HT-7)

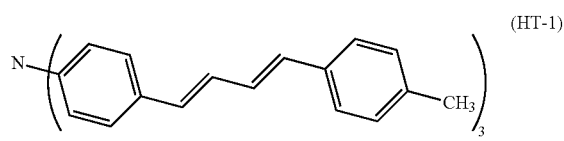

(HT-1)

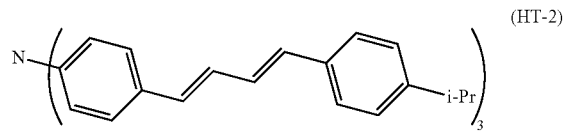

(HT-2)

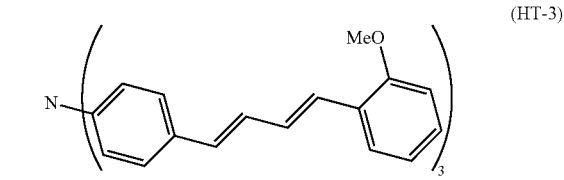

(HT-3)

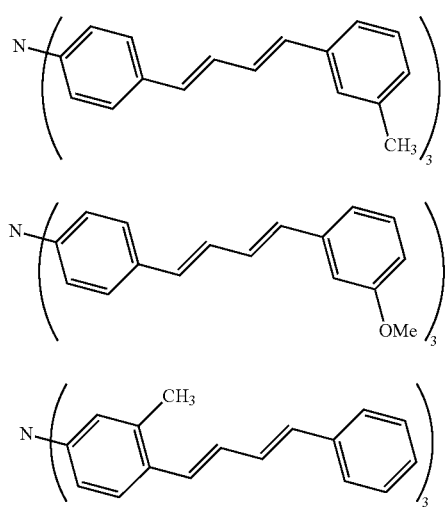

(HT-4)

(HT-5)

(HT-6)

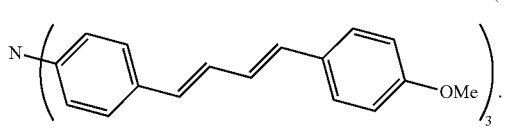

(HT-7)

5. An electrophotographic photosensitive member comprising
a photosensitive layer containing a charge generating material and a hole transport material, wherein
the photosensitive layer is either one of:
a multi-layer photosensitive layer including a charge generating layer that contains the charge generating material and a charge transport layer that contains the hole transport material, and in which the charge transport layer is located on the charge generating layer; and
a single-layer photosensitive layer containing the charge generating material and the hole transport material, and
the hole transport material is the triarylamine derivative according to claim 1.

* * * * *